(12) United States Patent
Manenti et al.

(10) Patent No.: US 10,179,914 B2
(45) Date of Patent: Jan. 15, 2019

(54) CDC25A INHIBITOR FOR THE TREATMENT OF DRUG RESISTANT CANCER OR FOR THE PREVENTION OF TUMOR RELAPSE

(71) Applicants: INSERM (INSTITUT NATIONAL DE LA SANTÉ ET DE LA RECHERCHE MÉDICALE), Paris (FR); UNIVERSITÉ PAUL SABATIER TOULOUSE III, Toulouse (FR)

(72) Inventors: Stéphane Manenti, Toulouse (FR); Sarah Bertoli, Toulouse (FR)

(73) Assignees: INSERM (INSTITUT NATIONAL DE LA SANTE ET DE LA RECHERCHE MEDICALE), Paris (FR); UNIVERSITE PAUL SABATIER TOULOUSE III, Toulouse (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/514,043

(22) PCT Filed: Sep. 28, 2015

(86) PCT No.: PCT/EP2015/072234
§ 371 (c)(1),
(2) Date: Mar. 24, 2017

(87) PCT Pub. No.: WO2016/046414
PCT Pub. Date: Mar. 31, 2016

(65) Prior Publication Data
US 2017/0247706 A1    Aug. 31, 2017

(30) Foreign Application Priority Data
Sep. 26, 2014 (EP) .................... 14306492

(51) Int. Cl.
| C12N 15/113 | (2010.01) |
| A61K 31/402 | (2006.01) |
| A61K 31/428 | (2006.01) |
| A61K 31/7088 | (2006.01) |
| A61K 31/713 | (2006.01) |
| A61K 45/06 | (2006.01) |

(52) U.S. Cl.
CPC ........ *C12N 15/1137* (2013.01); *A61K 31/402* (2013.01); *A61K 31/428* (2013.01); *A61K 31/7088* (2013.01); *A61K 31/713* (2013.01); *A61K 45/06* (2013.01); *C12Y 301/03048* (2013.01); *C12N 2310/14* (2013.01); *C12N 2320/31* (2013.01)

(58) Field of Classification Search
None
See application file for complete search history.

(56) References Cited

PUBLICATIONS

Weisberg et al. (Leukemia (2012) 26:2233-2244). (Year: 2012).*
Furukawa et al. (Leukemia (2007) 21:1005-1014). (Year: 2007).*
Thomadaki et al. (Ann.N.Y. Acad. Sci (2009) 1171:276-283). (Year: 2009).*
Marie-Christine Brezak et al: "IRC-083864, a novel bis quinone inhibitor of CDC25 phosphatases active against human cancer cells", International Journal of Cancer, vol. 124, No. 6, pp. 1449-1456, Mar. 15, 2009.
M.-C. Brezak: "Inhibition of human tumor cell growth in vivo by an orally bioavailable inhibitor of CDC25 phosphatases", Molecular Cancer Therapeutics, vol. 4, No. 9, pp. 1378-1387, Sep. 1, 2005.
Yoshimi Aoyagi et al: "A novel cinnamic acid derivative that inhibits CDC25 dual-specificity phophatase activity", Cancer Science, vol. 96, No. 9, pp. 614-619.
Fernandez-Vidal Anne et al: "Upregulation of the CDC25A phosphatase down-stream of the NPM/ALK oncogene participates to anaplastic large cell lymphoma enhanced proliferation", Cell Cycle, Landes Bioscience, US, vol. 8, No. 9, pp. 1373-1379.
Hirano N; Kohno J; Tsunoda S; Nishio M; Kishi N; Okuda T; Kawano K; Komatsubara S; Nakanishi N: "TMC-69, a new antitumor antibiotic with CDC25A inhibitory activity, produced by *Chrysosporium* sp. TC1068. Taxonomy, fermentation and biological activities.", Journal of Antibiotics, vol. 54, No. 5, pp. 421-427, May 1, 2001.
S. Kar: "PM-20, a novel inhibitor of CDC25A, induces extracellular signal-regulated kinase 1/2 phosphorylation and inhibits hepatocellular carcinoma growth in vitro and in vivo", Molecular Cancer Therapeutics, vol. 5, No. 6, pp. 1511-1519, Jun. 1, 2006.
M Levis et al: "FLT3: ITDoes matter in leukemia", Leukemia, vol. 17, No. 9, pp. 1738-1752, Sep. 1, 2003.

\* cited by examiner

*Primary Examiner* — J. E. Angell
(74) *Attorney, Agent, or Firm* — Whitham & Cook, PC

(57) ABSTRACT

The present invention concerns a CDC25A phosphatase inhibitor for use in the treatment of a drug resistant cancer and/or in prevention of tumor relapse in a patient suffering or having suffered from cancer.

Figure 1:
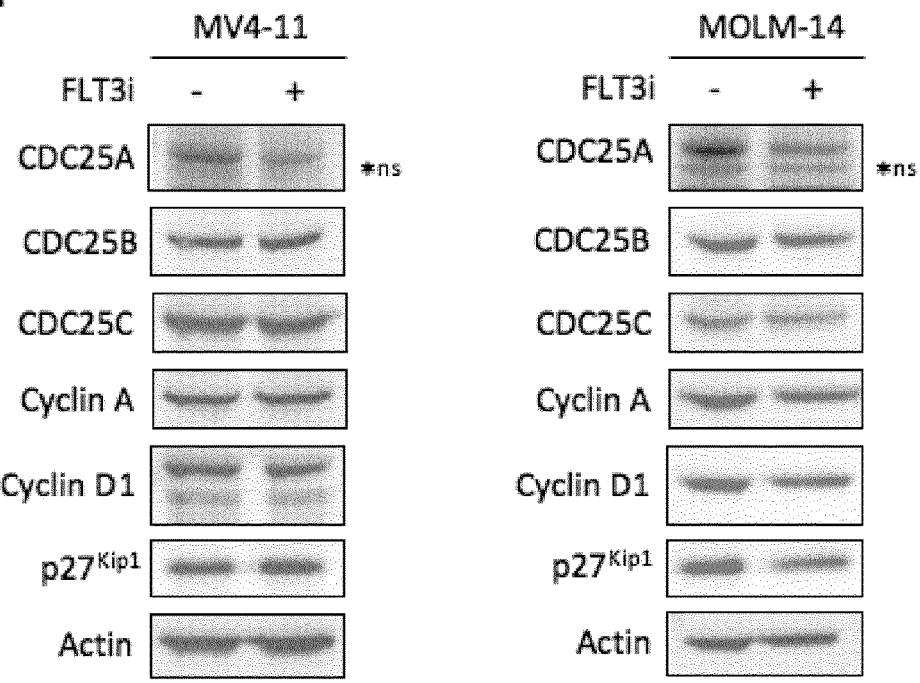
Figure 1:
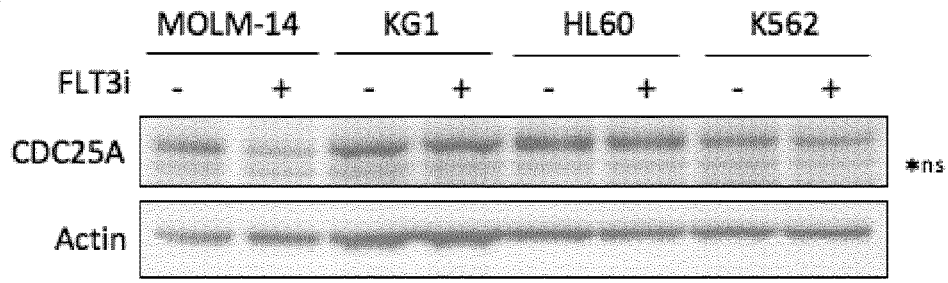

5 Claims, 19 Drawing Sheets a b

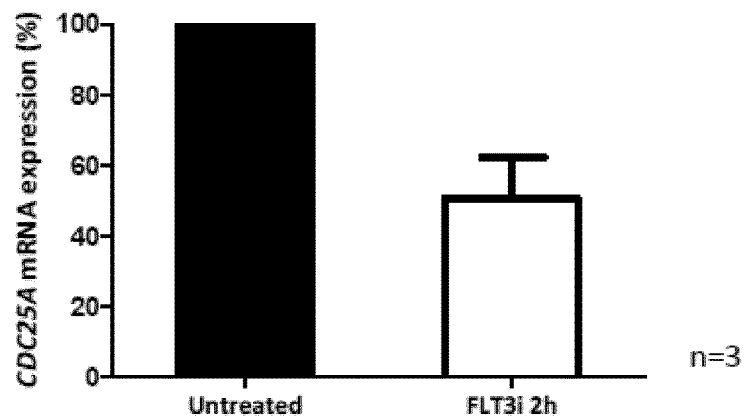
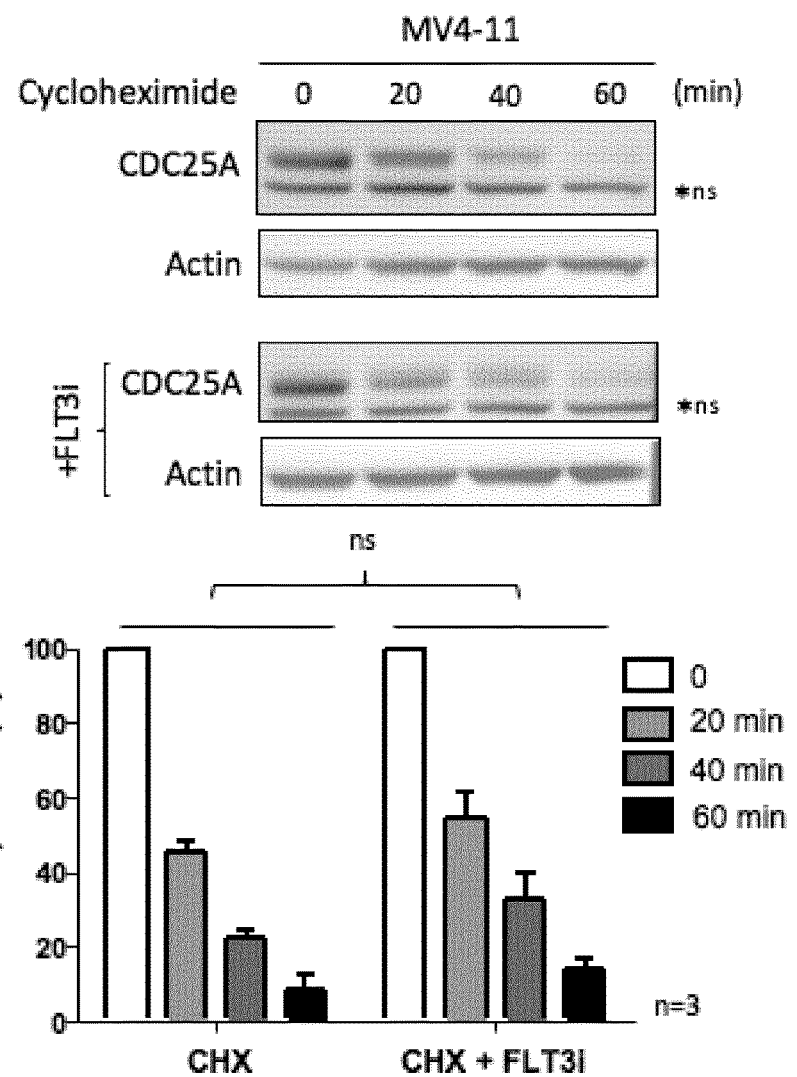
Figure 3B and C

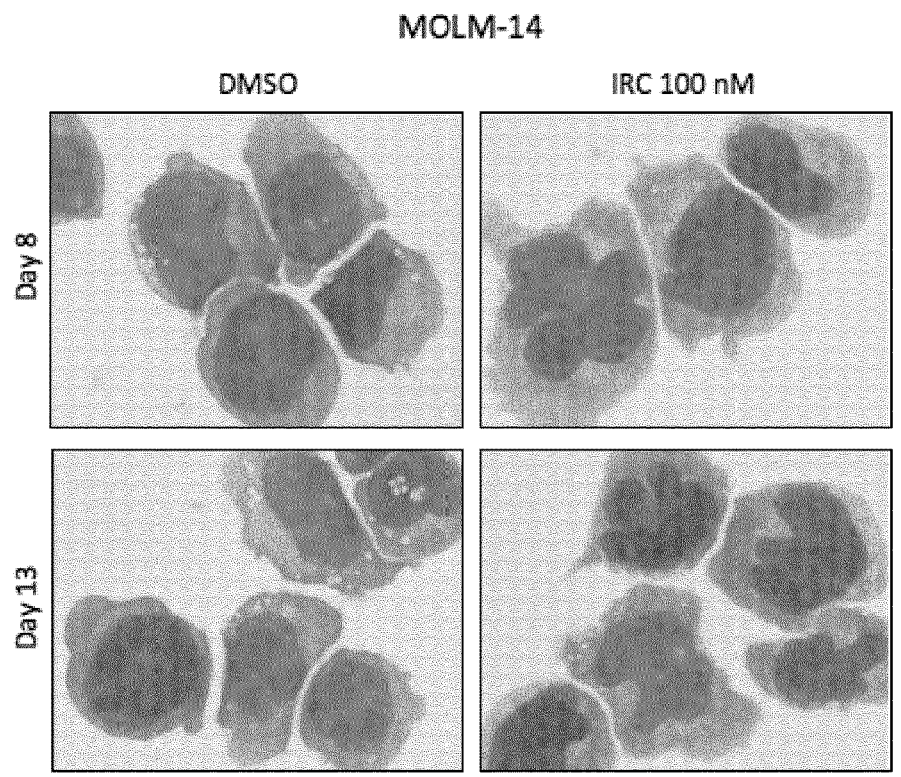
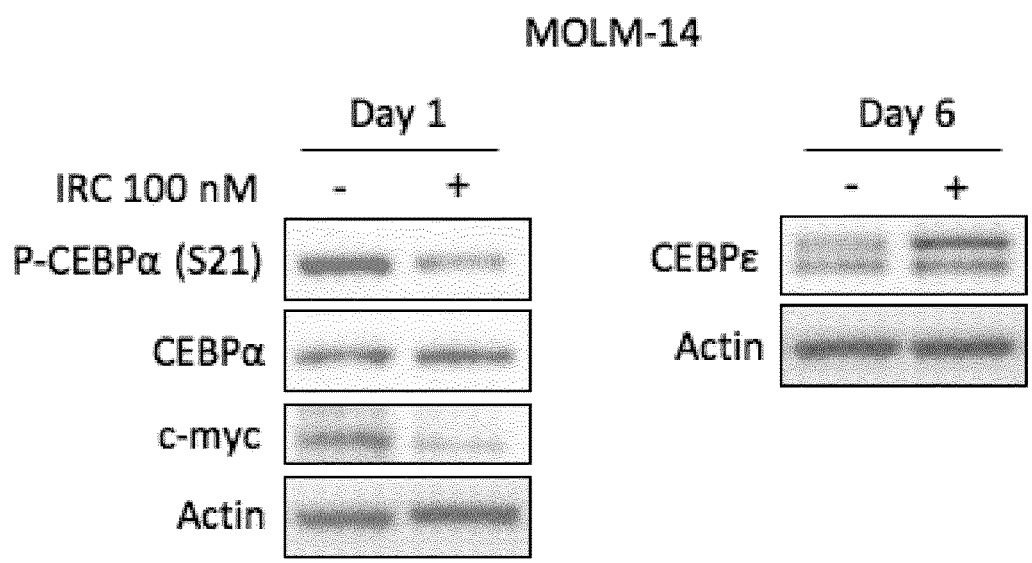
Figure 5C and D

CDC25A INHIBITOR FOR THE TREATMENT OF DRUG RESISTANT CANCER OR FOR THE PREVENTION OF TUMOR RELAPSE

RELATED APPLICATION

The present application claims priority to European Patent Application No. EP EP14306492.1, which was filed on Sep. 26, 2014. The European patent application is incorporated herein by reference in its entirety.

FIELD OF THE INVENTION

The present invention relates to a CDC25A phosphatase inhibitor for use in the treatment of a drug resistant cancer and/or in the prevention of tumor relapse in a patient suffering or having suffered from cancer.

BACKGROUND OF THE INVENTION

Acute myeloid leukemia (AML) is characterized by increased proliferation, cell death resistance and by a block of the hematopoietic process occurring at different stages of the myeloid differentiation (Meyer S C et al, Lancet Oncol 2014). The impact of several mutations has been explored this last decade, the most frequent being the internal tandem duplication (ITD) in the juxta-membrane domain of the Fms-Like Tyrosine kinase 3 (FLT3), which leads to constitutive activation of this receptor (Nakao M et al, Leukemia 1996). This mutation is particularly associated to normal karyotype AML (Thiede C et al, Blood 2002) and now is part to the most recent prognostic classification of AML (Döhner H et al, Blood 2010). During normal myeloid hematopoiesis, FLT3 is highly expressed and reported to play an important role at the granulo-monocyte progenitor level (Böiers C et al, Blood 2010).

Because of the high frequency of this mutation (25-30% of AML) and of its associated negative prognosis (Thiede C et al, Blood 2002 and Levis M et al, Leukemia 2003), several FLT3 inhibitors have been subsequently developed and tested in different clinical trials, either in combination with chemotherapy or in monotherapy (Wander S A et al, Ther Adv Hematol 2014; Stone R M et al, Leukemia 2012; Serve H et al, JCO 2013; Cortes J E et al, Blood 2012; Levis M J et al, Blood 2012 and Kampa-Schittenhelm K M et al, Mol Cancer 2013). These molecules have a negative impact on AML cells proliferation in vivo, and interestingly, their pro-differentiation effect was also reported clinically, suggesting that inhibiting FLT3-ITD could partially relieve the differentiation arrest occurring in this category of AML (Sexauer A et al, Blood 2012). Recent studies identified the ERK kinase and the cyclin-dependent kinase CDK1 as important players of FLT3-ITD AML differentiation arrest through phosphorylation of the C/EBPα transcription factor on its serine 21 (Zheng R et al, Blood 2004; Radomska H S et al, JExpMed 2006 and Radomska H S et al, JCI 2012), suggesting that CDK or ERK inhibitors could restore the differentiation program of these cells.

CDC25A is a dual specificity phosphatase involved in cyclin-dependent kinases activation during the cell cycle. CDC25A has important functions during replication and mitosis, as well as during the G1 phase of the cell cycle. CDC25A is finely regulated both at the transcription and protein levels (Fernandez-Vidal A et al, Anticancer Agents Med Chem 2008), and moderate variations of its cellular level affect genomic stability and oncogenic transformation process (Ray D et al, Cancer Research, 2008). CDC25A knock-out is lethal at an early stage of embryonic development. Its overexpression was described in different categories of cancers, and was often associated with an adverse prognosis (Boutros R et al, Nat Rev Cancer 2007). However, there is almost no study dealing with CDC25A status in AML or in other myeloid malignancies. CDC25A expression is increased by leukemic cells adhesion to fibronectin, and participates to the adhesion-dependent increased proliferation of these cells (Fernandez-Vidal A et al, Cancer Res 2006). CDC25A is also constitutively expressed downstream of oncogenic tyrosine kinases, including NPM-ALK and BCR-ABL (Fernandez-Vidal A et al, Cell Cycle 2010), as well as JAK2 V617F in myeloproliferative neoplasms (Gautier et al, Blood 2012).

In this invention, inventors demonstrate that CDC25A is an early target of FLT3-ITD oncogenic signaling, and is an important player of AML cells proliferation and differentiation arrest.

SUMMARY OF THE INVENTION

In a first embodiment, the invention relates to a CDC25A phosphatase inhibitor for use in the treatment of drug resistant cancer.

In a second embodiment, the invention relates to a CDC25A phosphatase inhibitor for use in the prevention of tumor relapse in a patient suffering or having suffered from cancer.

In a preferred embodiment, the drug resistant cancer according to the invention is associated with a mutated FLT3-ITD such as Acute Myeloid Leukemia (AML).

DETAILED DESCRIPTION OF THE INVENTION

The present invention arises from the finding by the inventors that CDC25A phosphatase inhibition reduces proliferation and induces monocytic differentiation of FLT3-ITD-positive AML cells in vitro and in vivo, and points at the central function of this phosphatase in the hematopoietic differentiation arrest of these cells. These inhibitors have proved to be effective in vitro in AML blasts and in vivo in AML xenografted tumors in mice. The inventors also show that the therapy induces cell differentiation of quiescent leukemia cells from patient.

Despite chemotherapy and allogenic stem-cell transplantation regimens, AML management remains a challenge since although the bulk of leukemic cells is usually sensitive to chemotherapy, relapses occur and conduct to death. AML resurgence results from the inefficacy of chemotherapy to effectively target quiescent leukemia-initiating cells (LIC) which are able to self-renew and propagate the disease (Bonnet and Dick, 1997; Terpstra et al., 1996). Therefore, therapies aimed at inducing cell differentiation of quiescent leukemia cells would be able to eradicate the disease and avoid tumor relapse.

The invention thus proposes a new targeted therapy for treating drug resistant disease and notably, drug resistant cancer. The invention is particularly advantageous for treating cancer expressing mutated FLT3-ITD, such as AML.

Definition

Throughout the specification, several terms are employed and are defined in the following paragraphs.

A "coding sequence" or a sequence "encoding" an expression product, such as an RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

As used herein, references to specific proteins (e.g., CDC25A) may include a polypeptide having a native amino acid sequence, as well as variants and modified forms regardless of their origin or mode of preparation. A protein that has a native amino acid sequence is a protein having the same amino acid sequence as obtained from nature (e.g., CDC25A). Such native sequence proteins may be isolated from nature or may be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including postranslational modifications. A native sequence protein includes proteins following post-translational modifications such as glycosylation, or phosphorylation, or other modifications of some amino acid residues.

Variants refer to proteins that are functional equivalents to a native sequence protein that have similar amino acid sequences and retain, to some extent, one or more activities of the native protein. Variants also include fragments that retain activity. Variants also include proteins that are substantially identical (e.g., that have 80, 85, 90, 95, 97, 98, 99%, sequence identity) to a native sequence. Such variants include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a native sequence protein (see, e.g., Creighton (1984) Proteins, W.H. Freeman and Company). In the case of substitutions, the amino acid replacing another amino acid usually has similar structural and/or chemical properties. Insertions and deletions are typically in the range of 1 to 5 amino acids, although depending upon the location of the insertion, more amino acids may be inserted or removed. The variations may be made using methods known in the art such as site-directed mutagenesis (Carter, et al. (1986) Nucl. Acids Res. 13:4331; Zoller et al. (1987) Nucl. Acids Res. 10:6487), cassette mutagenesis (Wells et al. (1985) Gene 34:315), restriction selection mutagenesis (Wells, et al. (1986) Philos. Trans. R. Soc. London SerA 317:415), and PCR mutagenesis (Sambrook et al., Molecular Cloning: A Laboratory Manual, 3rd edition, Cold Spring Harbor Press, N.Y., (2001)).

Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

The term "expression" when used in the context of expression of a gene or nucleic acid refers to the conversion of the information, contained in a gene, into a gene product. A gene product may be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs which are modified, by processes such as capping, polyadenylation, methylation, and editing, and proteins (e.g., EGFR) modified by, for example, methylation, acetylation, phosphorylation, ubiquitination, SUMOylation, ADP-ribosylation, myristilation, and glycosylation.

An "inhibitor of expression" refers to a natural or synthetic compound that has a biological effect in inhibiting the expression of a gene.

The term "CDC25 phosphatases" refers to protein phosphatases which belong, to the CDC25 family which are believed to be important regulators for the control of cell cycle progression by activating cyclin-dependent kinases (CDK). Three Cdc25 homologs have been found in mammals: Cdc25A, Cdc25B, and Cdc25C. Both Cdc25B and Cdc25C are thought to be regulators of G2/M transition through their ability to dephosphorylate and thus activate Cdk1, a component of the Cdk1/cyclin B mitotic kinase complex, which is required for cell entry into mitosis. Cdc25A is likely to be important for G1/S phase transition by dephosphorylating and thus activating Cdk2, 4, 6, which also form cyclin complexes, as well as in preserving genomic integrity, although Cdc25A may also have some role in the initiation of mitosis. The Cdc25s dephosphorylate Cdk/cyclins on pThr14 and/or on pTyr15 residues Cdc25 over-expression has been found in various human cancers, and is correlated with a more aggressive disease and poor prognosis. Cdc25B mRNA was first found to be over-expressed in cancer cell lines and SV40-transformed fibroblasts. Since then, Cdc25A and Cdc25B, but not Cdc25C, have been found to be overexpressed in various cancer tissues, including those of breast, ovarian, prostate, lung, colorectal, esophageal, thyroid, laryngeal, hepatocellular, gastric, pancreatic, endometrial, head and neck, neuroblastoma, glioma, and lymphoma. As activators of the cell cycle-controlling Cdks, the Cdc25 family of phosphatases are obvious-appreciated targets for anti-cancer therapy.

The term "CDC25A phosphatase inhibitor" refers to any CDC25A phosphatase inhibitor that is currently known in the art or that will be identified in the future, and includes any chemical entity that, upon administration to a patient, results in inhibition of a biological activity associated with the CDC25A phosphatase in the patient (in particularly the dephosphorylation of Cdk). Such CDC25A phosphatase inhibitor includes any agent (such as chemical entity and inhibitor of CDC25A expression) that blocks or inhibits CDC25A phosphatase activity. Such an inhibitor may act by binding directly to the CDC25A protein and inhibiting its phosphatase activity.

Examples of CDC25A phosphatase inhibitors include but are not limited to any of the CDC25A phosphatase inhibitors described in Garafalo S. et al. (Exp Opin. Ther Pat 2010 20(3):405-425) all of which are herein incorporated by reference.

The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

By "isolated" it is meant, when referring to a polypeptide (i.e. interferon) or a nucleotide sequence, that the indicated molecule is present in the substantial absence of other biological macromolecules of the same type.

The term "purified" as used herein means at least 75% by weight, more preferably at least 85% by weight, still preferably at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include additional bases or moieties which do not deleteriously affect the basic characteristics of the composition.

As used herein, the term "subject" denotes a mammal, such as a rodent, a feline, a canine, and a primate. Preferably a subject according to the invention is a human. Even more preferably a subject according to the invention is a human.

In the context of the invention, the term "treatment or prevention" means reversing, alleviating, inhibiting the progress of, or preventing the disorder or condition to which such term applies, or one or more symptoms of such disorder or condition. In particular, the treatment of the disorder may consist in reducing the number of malignant cells. Most preferably, such treatment leads to the complete depletion of the malignant cells.

"Drug resistance" as used in expressions such as "drug resistant cancer" or "drug resistant cells" or "drug resistant disease" means a circumstance where a disease (e.g., cancer) does not respond to a therapeutic agent. Drug resistance can be intrinsic, which means that the disease has never been responsive to the therapeutic agent, or acquired, which means that the disease ceases responding to the agent or agents to which the disease had previously been responsive. For cancers, such therapeutic agent may be a chemotherapeutic drug such as colchicine, vinblastine, doxorubicin, vinca alkaloids, etoposide, taxanes, or other small molecules used in cancer chemotherapy (Aracytine and Daunorubicin in LAM therapy) Drug resistance may be associated with cancer and other conditions, such as bacterial, viral, protozoal, and fungal diseases.

By "tumor relapse" or "cancer recurrence" is meant the return of cancer after treatment and after a period of time during which the cancer cannot be detected: in an another term it means reappearance of cancer after a disease-free period.

The terms "cancer" "malignancy" and "tumors" refer to or describe the pathological condition in mammals that is typically characterized by unregulated cell growth. In particular, the cancer may be associated with a solid tumor or unregulated growth of undifferentiated hematopoietic bone marrow cells (hematopoietic stem cell in particular). Examples of cancers that are associated with solid tumor formation include breast cancer, uterine/cervical cancer, oesophageal cancer, pancreatic cancer (Albrechtsson et al Pancreatology 2003), colon cancer, colorectal cancer, kidney cancer, ovarian cancer, prostate cancer, head and neck cancer, non-small cell lung cancer and stomach cancer. Preferably the solid tumor is breast cancer.

Preferably, the cancer or malignancy or tumor according to the invention is due to an unregulated growth of undifferentiated hematopoietic bone marrow cells (hematopoietic stem cell in particular).

As intended herein the expression "hematopoietic stem cell (HSC)" refers to adult multipotent stem cells that give rise to all the blood cell types including for example myeloid lineages (monocytes and macrophages, neutrophils, basophils, eosinophils), erythrocytes, megakaryocytes/platelets, and lymphoid lineages (T-cells, B-cells, NK-cells).

The expression "hematopoietic stem cell malignancy" or "hematopoietic malignancy" according to the invention comprises acute myeloid leukemia (AML), acute lymphoblastic leukemia, Chronic myeloid, lymphoid leukemia, lymphoma and myelodysplastic syndrome (as defined in 2008 WHO classification). Preferably, the hematopoietic malignancy according to the invention is selected from the group consisting of acute myeloid leukemia.

More preferably, the acute myeloid leukemia expresses the FLT3-ITD mutated tyrosine kinase receptor.

CDC25A Inhibitor for Use in the Treatment of Drug Resistant Cancer and/or in the Prevention of Tumor Relapse The present invention provides a CDC25A phosphatase inhibitor for use in the treatment of drug resistant cancer in a patient suffering from cancer.

The present invention also provides a CDC25A phosphatase inhibitor for use in the prevention of tumor relapse in a patient suffering or having suffered from cancer.

Typically, a CDC25A phosphatase inhibitor of the invention includes but is not limited to a
  i. quinone derivative (RC 083864 BN82685) or a maleimide derivative (PM20)
  ii. an inhibitor of CDC25A phosphatase expression A specific example of a CDC25A phosphatase inhibitor that may be used according to the present invention is PM20 (a maleimide derivative describes in WO2005081972 EP1722781 US2008039518 U.S. Pat. No. 7,504,430). PM-20 competitively inhibits Cdc25A, Cdc25B and Cdc25C with IC50 equal to 5, 10 and 40 µM, respectively. The maleimide derivatives are potent electrophilic entities, particularly for thiol selective modification. They are expected to react with and covalently bind to the protein phosphatase active site. Furthermore, PM20 inhibits the growth of human Hep 3B tumor cells (IC50=0.7 µM) at 10-fold lower concentrations than required to inhibit the growth of normal rat hepatocytes. PM20 and its derivatives appear to induce tyrosine phosphorylation of EGFR and extracellular signal regulated kinase, which are directly connected to the inhibition of tumor cell growth in vitro [Kar S, et al. Mol Cancer Ther 2006; 5:1511-9]. Cell cycle analysis reveals a block, mainly in the G1 phase of the cell cycle, which results in upregulation of CdK1, 2 and 4 tyrosine phosphorylation. When delivered intraperitoneally, PM20 also inhibits the growth of transplanted rat hepatoma cells (Fisher F344) in vivo [Kar S, et al. Mol Cancer Ther 2006; 5:1511-9].

PM20 is disclosed in WO2005081972 and has the following structure:

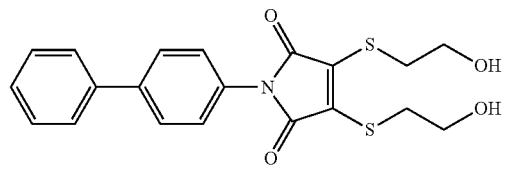 [SMILES: O=C1C(SCCO)=C(SCCO)C(=O)N1c1ccc(-c2ccccc2)cc1]

Another specific example of a CDC25A phosphatase inhibitor is the quinone derivative BN82685 a quinone-based Cdc25 inhibitor described by Brezak et al. [Mol Cancer Ther 2005; 4:1378-87].

BN82685 has the following structure:

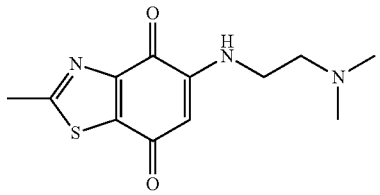

The effect of BN82685 on Cdc25 phosphatases is shown by an increase in phosphorylation on the tyrosine 15 residue of CdK1. BN82685 irreversibly inhibits the activity of purified recombinant Cdc25A, B and C with comparable potency (IC50=0.250, 0.250 and 0.171 µM, respectively). Cultured tumor cell proliferation studies show that a relatively short treatment time (1 h) inhibits proliferation for 96 h. A large panel of human cell lines was tested for sensitivity to BN82685. In addition, BN82685-mediated growth inhibition was unaffected by classical resistance mechanisms that involve drug efflux pumps, such as P-glycoprotein or multi-drug resistance proteins. Moreover, BN82685 impaired microtubule dynamics and delayed mitotic spindle assembly, probably by inhibition of CdK dependent phosphorylation of key cytoskeleton regulatory proteins. Finally, BN82685 inhibited the growth of Mia-Paca-2 tumors xenografted into nude mice. BN82685 is one of the few inhibitors of CDC25 that was active in vivo after oral administration.

Another specific example of CDC25A phosphatase inhibitor that is used according to the present invention is the quinone derivative IRC 083864 (WO2006067311 EP1831209 JP2008524175).

IRC 083864 has the following structure:

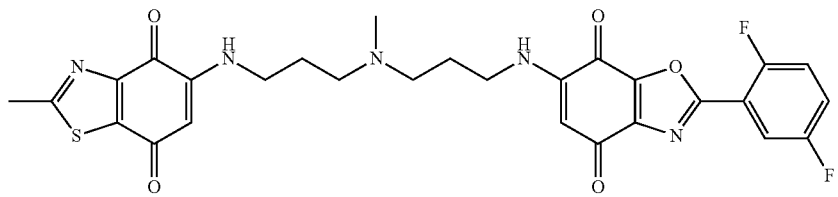 [SMILES: Cc1nc2c(s1)C(=O)C=C(NCCCN(C)CCCNC1=CC(=O)c3nc(-c4cc(F)ccc4F)oc3C1=O)C2=O]

IRC 083864 a bis-quinonoid Cdc25 inhibitor was evaluated in models of human cancer in vitro and in vivo. IRC-083864 inhibited several Cdc25 enzyme types (A, B2, B3 and C) with IC50 values in the nanomolar range. Interestingly, despite the large molecular size of IRC 083864, which may reduce its ability to penetrate cell membranes, it inhibits tumor cell proliferation with a potency equivalent to that of BN82685. It irreversibly inhibits cell proliferation and cell cycle progression and prevents entry into mitosis. In addition, IRC 083864 inhibits the growth of HCT-116 tumor spheroids by induction of p21 and apoptosis. Delivered via intravenous and oral routes, IRC-083864 reduces the growth of human Mia Paca-2 and LNCaP xenografts with an efficacy comparable to currently tested references. Similar results were observed in HT29 colon tumor cells compared to the topoisomerase inhibitor CPT-11 and in HL60 leukemia cells compared to adriamycine. No sign of apparent toxicity was observed at this stage of the study or with these regimens Additional non-limiting examples of CDC25A phosphatase inhibitor include any of the CDC25A phosphatase inhibitor described in Garafalo S. et al. (Exp Opin. Ther Pat 2010 20(3):405-425), all of which are herein incorporated by reference IRC 083864 are preferred CDC25A phosphatase inhibitor that may be used within the frame of the present invention. The dose used for IRC 083864 is from 1 to 10 microM, preferably from 2.5 microM to 5 micro M.

In preferred embodiment, the CDC25A phosphatase inhibitor is IRC 083864.

Tests for determining the capacity of a compound to be CDC25A phosphatase inhibitor are well known to the person skilled in the art. In a preferred embodiment, the inhibitor specifically binds to CDC25 in a sufficient manner to inhibit the phosphatase activity of CDC25A. Binding to CDC25A and inhibition of the phosphatase activity of CDC25A may be determined by any competing assays well known in the art. For example the assay may consist in determining the ability of the agent to be tested as CDC25A phosphatase inhibitor to bind to CDC25A. The binding ability is reflected by the Kd measurement. The term "KD", as used herein, is intended to refer to the dissociation constant, which is obtained from the ratio of Kd to Ka (i.e. Kd/Ka) and is expressed as a molar concentration (M). KD values for binding biomolecules can be determined using methods well established in the art. In specific embodiments, an inhibitor that "specifically binds to CDC25A" is intended to refer to an inhibitor that binds to human CDC25A polypeptide with a KD of 1 µM or less, 100 nM or less, 10 nM or less, or 3 nM or less. Then a competitive assay may be settled to determine the ability of the agent to inhibit phosphatase activity of CDC25A. The functional assays may be envisaged such evaluating the phosphorylation of the CDC25A substrate (i.e. CDK1 or CDK2). Such functional test are described in Brezac et al (Mol Cancer Ther. 2005 September; 4(9):1378-87) or Brezac et al (Cancer Res. 2004 May 1; 64(9):3320-5).

Preferably, inhibition of the phosphorylation of the CDC25A substrate in the presence of the inhibitor must be observed in a dose-dependent manner and the measured signal is at least 10% lower, preferably at least 50% lower than the signal measured with a negative control under comparable conditions. Preferably, the inhibitor according to the invention exhibits an IC50 of at least 1 µM, preferably 100 nM as measured in at least one of the assays described above.

According to the invention, the inhibitor of CDC25A phosphatase provides the advantage of inhibiting proliferation and re-inducing differentiation of tumor cells which are valuable for the treatment of drug resistant cancer and/or for use in the prevention of a tumor relapse in a patient suffering or having suffered from cancer.

Another aspect of the invention is an inhibitor of CDC25A phosphatase expression for use in the treatment of drug resistant cancer in a patient suffering from cancer and/or for use in the prevention of tumor relapse in a patient who suffers or has suffered from cancer.

Inhibitors of CDC25A phosphatase expression for use in the present invention may be based on antisense oligonucleotide constructs. Anti-sense oligonucleotides, including anti-sense RNA molecules and anti-sense DNA molecules, act to directly block the translation of CDC25A phosphatase mRNA by binding thereto and thus preventing protein translation or increasing mRNA degradation, thus decreasing the level of CDC25A phosphatase proteins, and their activity, in a cell. For example, antisense oligonucleotides of at least about 15 bases and complementary to unique regions of the mRNA transcript sequence encoding CDC25A phosphatase may be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) may also function as inhibitors of CDC25A phosphatase expression according to the present invention. CDC25A phosphatase gene expression may be reduced by contacting the tumor, subject or cell with a small double stranded RNA (dsRNA), or a vector or construct causing the production of a small double stranded RNA, such that CDC25A phosphatase expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes may also function as inhibitors of CDC25A phosphatase expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of CDC25A phosphatase mRNA sequences are thereby useful within the scope of the present invention. Specific ribozyme cleavage sites within any potential RNA target are initially identified by scanning the target molecule for ribozyme cleavage sites, which typically include the following sequences, GUA, GuU, and GUC. Once identified, short RNA sequences of between about 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using, e.g., ribonuclease protection assays.

Both antisense oligonucleotides and ribozymes useful as inhibitors of CDC25A phosphatase expression may be prepared by known methods. These include techniques for chemical synthesis such as, e.g., by solid phase phosphoramadite chemical synthesis. Alternatively, anti-sense RNA molecules may be generated by in vitro or in vivo transcription of DNA sequences encoding the RNA molecule. Such DNA sequences may be incorporated into a wide variety of vectors that incorporate suitable RNA polymerase promoters such as the T7 or SP6 polymerase promoters. Various modifications to the oligonucleotides of the invention may be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing CDC25A phosphatase. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One may readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus may be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus may integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus may also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, may express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid may be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Pharmaceutical Composition and Therapeutic Method

The present invention also provides a pharmaceutical composition comprising:

A CDC25A inhibitor; and a pharmaceutically acceptable carrier and optionally an additional chemotherapeutic drug.

for use in the treatment of a patient suffering from drug resistant cancer and/or in the prevention of tumor relapse in a patient suffering or having suffered from cancer.

The expression "pharmaceutically acceptable carrier" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen according to the invention depend upon the condition to be treated, the severity of the illness, the age, weight, and sex of the patient, etc.

Pharmaceutical compositions formulated in a manner suitable for administration to humans are known to the skilled in the art. The pharmaceutical composition of the invention may further comprise stabilizers, buffers, etc.

The compositions of the present invention may, for example, be formulated and used as tablets, capsules or elixirs for oral administration, suppositories for rectal administration, sterile solutions or suspensions for administration by injection.

The choice of the formulation ultimately depends on the intended way of administration, such as e.g. an intravenous, intraperitoneal, subcutaneous or oral way of administration, or a local administration via tumor injection.

The pharmaceutical composition according to the invention may be a solution or suspension, e.g. an injectable solution or suspension. It may for example be packaged in dosage unit form.

The pharmaceutical composition according to the invention may be used in the treatment of drug resistant cancer or in prevention of tumor relapse in a patient suffering or from cancer. Preferably, the cancer drug resistant cancer is solid tumor or a hematopoietic malignancy.

In one embodiment, drug resistant cancer is a solid tumor selected from the group consisting of: breast cancer, pancreatic cancer, ovary cancer, head-and-neck cancer, colon cancer, colorectal cancer, prostate cancer, stomach cancer and non-small-cell lung carcinoma.

In one embodiment hematopoietic malignancy is acute myeloid leukemia.

More preferably, the acute myeloid leukemia expresses the FLT3-ITD mutated tyrosine kinase receptor.

In a preferred embodiment, the CDC25A inhibitor is IRC 083864.

The present invention further provides a method of treating drug resistant cancer in an individual in need thereof, said method comprising the step of administering an effective amount of:
  CDC25A phosphatase inhibitor (as defined here above); and
  optionally a chemotherapeutic drug that is an anti-mitotic agent;
  to an individual in need thereof.

In one embodiment drug resistant cancer is acute myeloid leukemia.

More preferably, the acute myeloid leukemia expresses the FLT3-ITD mutated tyrosine kinase receptor.

By a "chemotherapeutic drug" is meant a drug that has proved its efficacy for the treatment of cancer, namely a drug having a marketing approval or a drug undergoing clinical or preclinical trial for the treatment of cancer.

By an "anti-mitotic agent", also referred as a "spindle poison" or a "mitosis poison", is meant an agent that is capable of slowing down and/or inhibiting mitosis. Such anti-mitotic agents can for example stabilize tubulin and thus "freeze" the mitosis process (as in the case of most taxanes), or destroy mitotic spindles (as in the case of most *vinca* alkaloids).

In a preferred embodiment, the chemotherapeutic drug is a taxane. The taxanes are diterpenes that were originally derived from plants of the genus *Taxus*. Now, they are usually synthesized. Taxanes have been used to produce various chemotherapy drugs such as, e.g., paclitaxel (Taxol), docetaxel (Taxotere) and cabazitaxel. These taxanes, and especially paclitaxel (Taxol), are preferred chemotherapeutic drugs that can be used in the frame of the present invention.

Alternatively, the chemotherapeutic drug may be a *vinca* alkaloid such as, e.g., vinblastine, vincristine, vindesine or vinorelbine.

The chemotherapeutic drug may also be an anti-mitotic agent that is neither a taxane nor a *vinca* alkaloid, such as e.g., colcemid, colchicine or nocodazole.

The drugs are administered in an "effective amount", i.e. in an amount sufficient to treat the cancer. It will be appreciated that this amount will vary with the effectiveness of therapeutic agent(s) employed, with the nature of any carrier used, with the seriousness of the disease and the age of the patient. The determination of appropriate amounts for any given composition is within the skill in the art, through standard series of tests designed to assess appropriate therapeutic levels.

By "individual in need thereof" is meant an individual suffering or having suffered from cancer, more specifically from drug resistant cancer or an individual that is in remission after having suffered from cancer.

In the frame of the present invention, the individual preferably is a human individual.

The term "treating" is meant to encompass both therapeutic and prophylactic methods, i.e. a method aiming at curing, improving the condition and/or extending the lifespan of an individual suffering or having suffered from the cancer. More specifically from drug resistant cancer. It also refers to methods aiming at preventing the tumor relapse in a patient suffering or having suffered from cancer.

The invention will be further illustrated by the following figures and examples. However, these examples and figures should not be interpreted in any way as limiting the scope of the present invention.

FIGURES

FIG. 1. CDC25A is an early cell cycle target downstream of FLT3-ITD.

(a) MV4-11 (left panel) and MOLM-14 (right panel) FLT3-ITD expressing cells were treated for 2 hours with FLT3 inhibitor III (100 nM), and the protein levels of CDC25A, CDC25B, CDC25C, Cyclin A, Cyclin D1 and p27Kip1 were analyzed by western blot. (b) MOLM-14 (FLT3-ITD postive), KG1 and HL-60 (FLT3 wt positive) and K562 (FLT3 negative) cell lines were treated for 2 hours with FLT3 inhibitor III and the level of CDC25A was analyzed by western blot. Actin was used as a loading control. These results are representative of three independent experiments. ns: non specific.

Figure 2:
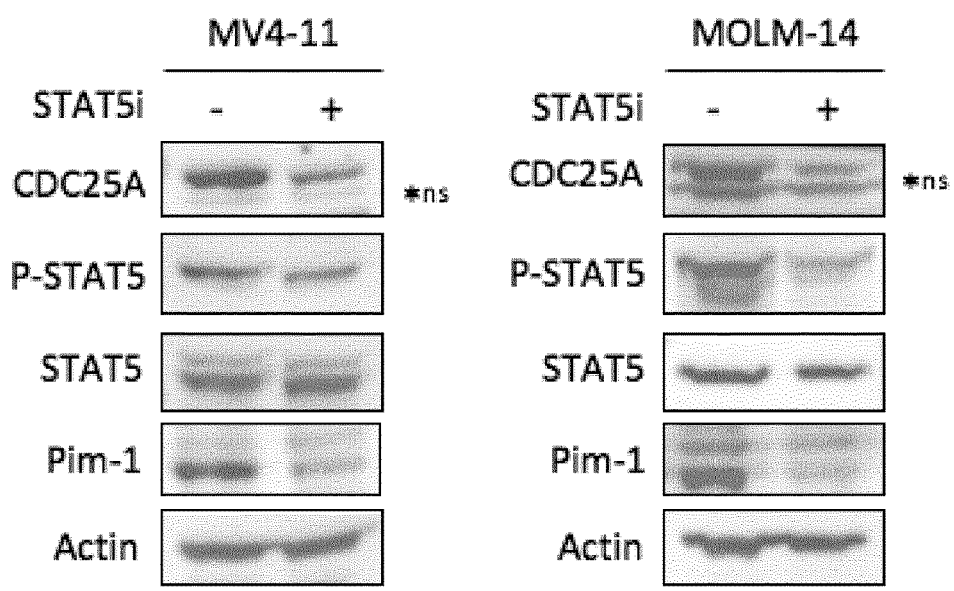
Figure 2:
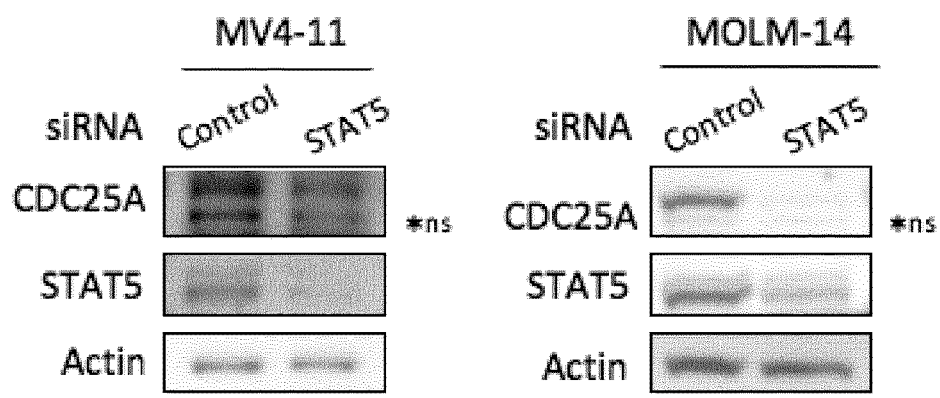

FIG. 2. STAT5 regulates CDC25A downstream of FLT3-ITD.

(a) MV4-11 (left panel) and MOLM-14 (right panel) cells were treated for 2 hours with STAT5 inhibitor (100 nM). CDC25A, Pim1, and STAT5 protein and phosphorylation levels were analyzed by western blot. (b) MV4-11 and MOLM-14 cells were transfected for 24 hours with STAT5A/B siRNA and the impact on CDC25A protein level was analyzed by western blot. These results are representative of three independent experiments. Actin was used as a loading control in these experiments. ns: non specific.

Figure 3:
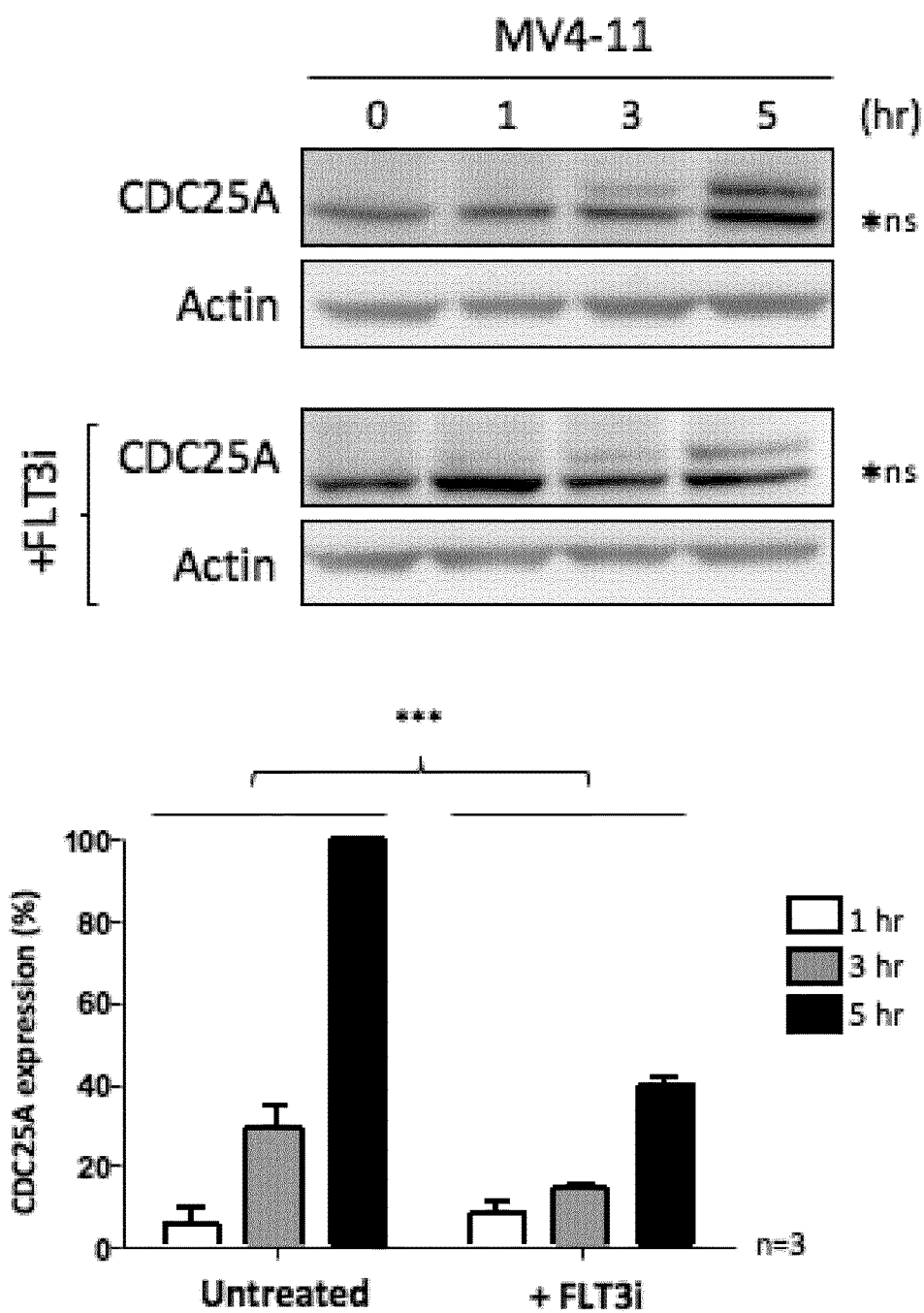

FIG. 3. FLT3-ITD regulates CDC25A protein synthesis and mRNA level.

(a) MV4-11 cells were first treated by cycloheximide (50 µg/mL) for 90 minutes in order to completely down regulate CDC25A. Cells were then placed in normal culture conditions in the presence (lower panel) or the absence (upper panel) of FLT3 inhibitor (100 nM), and western blot analysis of CDC25A was performed at the indicated times. The FLT3 inhibitor was added 30 minutes before medium wash. This western blot is representative of three independent experiments. The right panel shows the quantification of three independent experiments. (b) CDC25A mRNA expression was measured by quantitative RT-PCR after FLT3 inhibition for 2 hours (100 nM). The graph shows the mean+/−SEM of CDC25A mRNA expression in untreated and treated cells, in three independent experiments. (c) MV4-11 cells were treated with cycloheximide (50 µg/mL) for the indicated times. FLT3 inhibitor III (100 nM) was added 30 minutes before cycloheximide treatment, and left in the medium. This western blot is representative of three independent experiments. The right panel shows the quantification of three independent experiments. ns: non specific.

FIG. 4. CDC25A is an important determinant of FLT3-ITD leukemic cells proliferation.

(a) MV4-11 and MOLM-14 FLT3-ITD positive cells, KG1, HL-60 and TF-1 FLT3 wild type cells, and K562 FLT3 negative cells were cultured in the presence of the CDC25 inhibitor IRC-083864 (200 nM). Cells were harvested each day and counted after trypan blue coloration. The graph represents three independent experiments.

(b) MOLM-14 and MV4-11 cells were transfected with CDC25A siRNA for 24 hours, and cells were counted after trypan blue coloration (upper panel). The efficiency of CDC25A siRNA was estimated by western blot analysis (lower panel). ns: non specific.

(c) Primary cells from patients were cultured in semi-solid medium to estimate their clonogenic potential as described in the Methods section, in the presence or the absence of IRC-083864 (100 and 200 nM). 6 FLT3-ITD positive (upper panel) and 4 FLT3-wild type (lower panel) AML primary samples were used for these experiments. Leukemic colonies were scored under an inverted microscope at day 7.

(d) MOLM-14, and MOLM-14 TKD cells, were grown in the presence of AC-220 1 nM (upper panel) or IRC-083864 200 nM (lower panel). Cells were harvested each day and counted after trypan blue staining. The graphs represent three independent experiments.

FIG. 5. CDC25 inhibition relieves differentiation block in FLT3-ITD AML cell lines.

(a-b) MOLM-14 and MV4-11 cells were treated for different times with IRC-083864 (100 nM and 200 nM) and the expression of the cell surface markers CD11b, CD14 and CD15 were followed by flow cytometry analysis. (c) MOLM-14 and MV4-11 cells were treated for different times with IRC-083864 (100 nM) and morphological changes were estimated by microscopy after cells were cytospun and stained at days 8 and 13. Original magnification ×100. (d) MOLM-14 cells were treated for different times with IRC-083864 (100 nM) and c-myc expression as well as C/EBPα phosphorylation on serine 21 were analyzed by western blot at day 1, and C/EBPε expression after 6 days of treatment. (e) MOLM-14 cells were transfected with CDC25A shRNA The expression of the cell surface markers CD11b, CD14 and CD15 were followed by flow cytometry analysis at day 3 and 6 (upper panel), and their morphology was analyzed by microscopy after 6 days (lower panel). Original magnification ×100. (f) MOLM-14 cells were transfected with CDC25A siRNA, and their morphology was analyzed by microscopy after 3 days (upper panel). Original magnification ×100. The efficiency of CDC25A siRNA was assessed by western blot analysis (lower panel). These results are representative of three independent experiments. ns: non specific FIG. 6. CDC25 inhibition relieves differentiation block in FLT3-ITD AML primary cells from patients.

(a) 4 primary samples from patients carrying the FLT3-ITD mutation (ITD #1-4) were treated for 6 days with IRC-083864 (100 nM), and the expression of CD14 (upper panel) and CD15 (lower panel) was followed by flow cytometry analysis. (b) Quantification (mean±SEM, n=4) of CD14 and CD15 expression in response to IRC-083864. (c)

The morphology of primary cells from patients used in (a) was analyzed by microscopy after 6 days and 9 days of treatment with IRC-083864. Original magnification ×100.

Figure 7A:
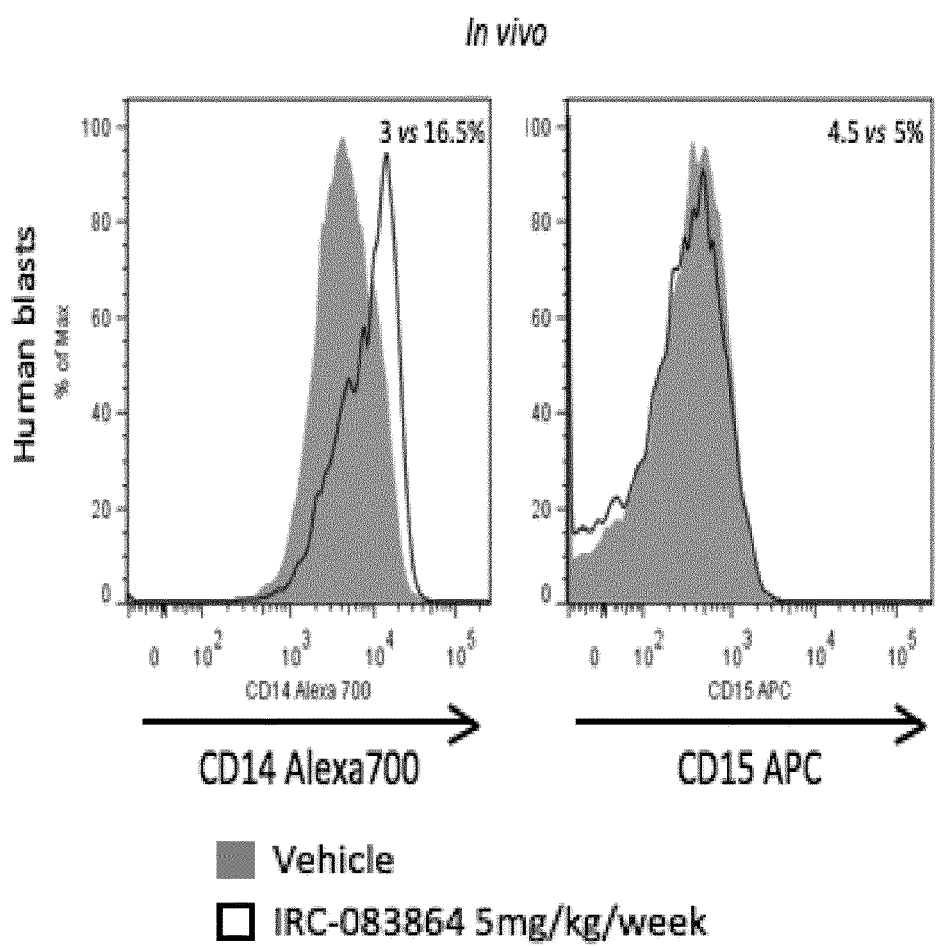
Figure 7B:
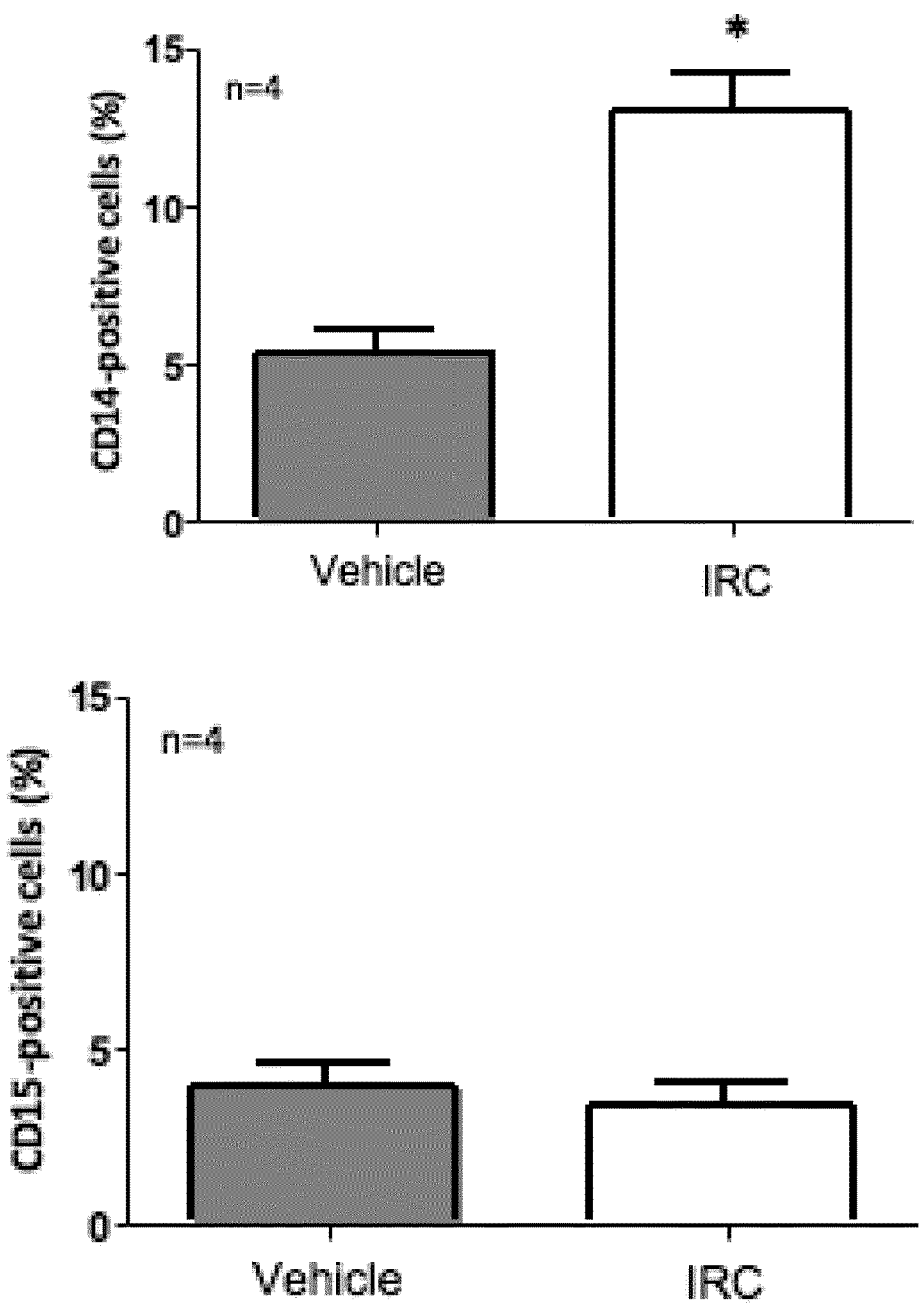

FIG. 7. CDC25A inhibition induces differentiation of FLT3-ITD AML cells in vivo (a) NSG mice were injected with 2 millions MOLM-14 cells, and treated with IRC-083864 at 5 mg/kg/week i.p. (n=4) or with vehicle buffer (n=4) as described in the Methods section. Bone marrow cells were extracted after dissection after two weeks and the expression of CD14 and CD15 on human blasts was followed by flow cytometry analysis. (b) Quantification (mean±SEM, n=4) of CD14 and CD15 expression in response to IRC-083864. (c) Morphological analyses of human cells used in (a). Original magnification ×100.

EXAMPLE

Methods

Cell lines and reagents. Human acute myeloid leukemia cell lines MOLM-14 (Matsuo Y et al, Leukemia 1997) (kindly provided by Martin Carroll, University of Pennsylvania, Philadelphia, Pa., USA) MV4-11, K562 (ACC-102 and ACC-10, DSMZ, Braunschweig, Germany) and FLT3-ITD-expressing murine BaF3 cells were cultured in RPMI 1640 medium (Gibco, Life Technologies, Carlsbad, Calif., USA) supplemented with 10% fetal bovine serum (Sigma, Saint Louis, Calif., USA). TF-1 (ATCC-CRL2003) cells were cultured in RPMI 1640 medium with 10% fetal bovine serum and GM-CSF 2 ng/ml. Concerning MOLM-14 cell line, the presence of a monoallelic 21 bp FLT3-ITD mutation and of an MLL-containing ins(11; 9)(q23;p22p23) were verified (Hematology laboratory of Toulouse University Hospital, Prof E. Delabesse and Dr I. Luquet). KG1 and HL-60 (ACC-14 and ACC-3, DSMZ) cell lines were grown in Iscove's Modified Dulbecco's Medium (IMDM, Gibco) plus 20% FBS. All cells were grown in the presence of 100 units/ml of penicillin and streptomycin (Invitrogen) at 37° C. and 5% CO2.

The FLT3 inhibitor III (Furet P et al, J Med Chem 2006), Akt inhibitor VIII and STAT5 inhibitor were purchased from Calbiochem (San Diego, Calif., USA). The FLT3 inhibitor quizartinib AC220 and the MEK inhibitor PD0325901 were purchased from Selleck Chemicals (Houston, Tex., USA). The CDC25 inhibitor IRC-084864 (Brezak M C et al, Int J Cancer 2009) was kindly provided by IPSEN laboratory (Marie-Odile Contour-Galcera, Les Ulis, France) and NSC-95397 was purchased from Enzo Life Sciences (Farmingdale, N.Y., USA) (Lazo J S et al, Mol Pharmacol 2002). The translation inhibitor cycloheximide was purchased from Sigma (Saint Louis, Mo., USA). The proteasome inhibitor bortezomib was kindly provided by Clement Larrue (CRCT Team 18, Toulouse, France). hFLT3 ligand, hGM-CSF, hG-CSF and hIL-3 were purchased from R&D Systems Inc (Minneapolis, Minn., USA).

Patient samples. Patient AML samples were obtained after informed consent in accordance with the Declaration of Helsinki and stored at the HIMIP collection. According to the French law, HIMIP collection has been declared to the Ministry of Higher Education and Research (DC 2008-307 collection 1) and obtained a transfer agreement (AC 2008-129) after approbation by ethical committees (Comité de Protection des Personnes Sud-Ouest et Outremer II and APHP ethical committee). Clinical and biological annotations of the samples have been declared to the CNIL (Comité National Informatique et Libertés i.e. Data processing and Liberties National Committee). Frozen cells were thawed in IMDM medium with 20% FBS and immediately processed for treatment. All patients were diagnosed at the Department of Hematology of Toulouse University Hospital. Their characteristics are summarized in Table 1.

Co-cultures. Patient samples, containing at least 80% of blasts, were co-cultured with murine stromal cells (MS-5 (ACC-441) kindly provided by Helena Boutzen, CRCT Team 18, Toulouse, France) in IMDM (Gibco) supplemented with 15% BIT (Stem Cell Technologies, Vancouver, BC, Canada), 100 units/ml penicillin and streptomycin (Invitrogen), 5 µM β-mercaptoethanol (Invitrogen), 1 mM pyruvate (Sigma), MEM 1× (Sigma), 100 ng/mL DNase (MP Biomedicals, Solon, Ohio, USA), 10 ng/mL hIL-3, 100 ng/mL hSCF, and 10 ng/ml hTPO (all from R&D Systems Inc, Minneapolis, Minn., USA). All the samples were then processed for treatment with the different reagents (IRC-083864 or NSC-95397).

siRNA. The MV4-11 cell line was transfected with the Amaxa nucleofection technology (Lonza, Koeln, Germany). Cells (2×106) were resuspended in 100 µL of Amaxa solution L. 300 nM of specific STAT5A and STAT5B siRNA (ON-TARGETplus SMARTpool, human STAT5A and STAT5B, Dharmacon) or total CDC25A siRNA (Hs_CDC25A_9, Qiagen, Hilden, Germany) or 3'UTR CDC25A siRNA (CDC25A 2943, Sigma) or negative control (si genome control pool non targeting #2, or ON-TARGETplus control pool (Dharmacon)) were added, and cells were transfected with the nucleofector device (program Q-001; solution V and program O-017 for MOLM-14; solution R and program V-001 for KG1). Cells were subsequently resuspended in normal culture medium at a concentration of 5×105 cells/mL. Twenty-four or forty-eight hours after transfection, cells were counted (trypan blue staining), and western blotting was performed.

Lentiviral infections. To generate lentiviral vectors expressing CDC25A protein, sequences were cloned into the pTrip-TAL-Ires-GFP lentiviral vector. We used 293-T packaging cells, co-transfected with lentiviral protein (GAG, POL, and ENV) encoding plasmids, and plasmids containing a control or CDC25A genes, separately. Supernatants containing lentivirus were collected 48 h after transfection, during 3 consecutive days. MOLM-14 cells were plated at 5×105 cells in 200 µl in serum-free medium and 5 µl of lentiviral supernatant was added during 3 h. Cells were then grown in 10% FBS RPMI medium.

Western blot. 2×106 cells were usually lysed in 100 µL of NuPAGE® LDS Sample Buffer (Novex, Life Technologies, Carlsbad, Calif., USA), sonicated for 15 seconds, and boiled for 3 minutes. Proteins were then resolved on NuPAGE® 4-12% Bis-Tris Gels and transferred to nitrocellulose membrane. Saturation of the membrane was done for 1 hour in Tris Buffer Saline with Tween 0.1% (TBS-T) containing 5% non-fat milk or 5% bovine serum albumin. Membranes were blotted with proper antibodies overnight at 4° C., washed thrice with TBS-T, and incubated for 30 minutes with HRP-conjugated secondary antibody (Promega, Madison, Wis., USA). After three additional washes, detection was achieved with Supersignal West Pico Chemiluminescent substrate (Thermo Fisher Scientific, Rockford, Ill., USA). The antibodies used were: monoclonal anti-CDC25A (F-6), anti-Cyclin D1 (HD11), anti-Pim1 (12H8), anti-c-myc (9E10), and polyclonal anti-CDC25B (C-20), anti-CDC25C (C-20), anti-Cyclin A (C-19), and anti-Akt1/2/3 (H-136), from Santa Cruz Biotechnology (Santa Cruz, Calif., USA), monoclonal anti-phospho-p44/42 MAPK (Erk1/2) (Thr202/Tyr204) (E10) and polyclonal anti-phospho-STAT5 (Tyr 694), anti-STAT5, anti-p44/42 MAPK, anti-phospho-Ser473

Akt (D9E) XP, anti-phospho-Cdc2 (Tyr15), anti-phospho-C/EBPα (Ser21), anti-C/EBPα (p42) and anti-C/EBPε (C-22) from Cell Signaling Technology (Beverly, Mass., USA), anti-p27KIP1 from BD Biosciences (San Diego, Calif., USA); anti-β-actin and anti-α-tubulin from Sigma.

Quantitative RT-PCR. Total RNA was extracted by RNeasy Kit (Qiagen) according to the manufacturer. RNA quality and purity was assessed by using the Agilent RNA 6000 Nano kit (Agilent Technologies, Santa Clara, Calif., USA). cDNA was generated with the SuperScript III First-Strand Synthesis System for RT-PCR (Invitrogen) following the manufacturer instructions. The PCR was performed with TaqMan® Gene Expression Master Mix (Applied Biosystems, Foster City, Calif., USA) with 1 µl of cDNA on a LightCycler®480 (Roche). The primer used was Hs00947994_m1 (Applied Biosystem) for CDC25A. GUSB (Hs00939627_m1) and B2M (Hs00984230_m1) were used as housekeeping genes. Results were analyzed with the LightCycler®480 software release 1.5.0 SP4 using the conventional $\Delta\Delta Ct$ method.

Flow cytometry. Apoptotic cells were detected with Annexin V-FITC detection kit from BD Pharmingen (San Diego, Calif., USA) according to the manufacturer instructions. To evaluate AML cell differentiation, cells were stained for 30 min with the following anti-human monoclonal antibodies: CD11b-PE (Beckman Coulter), CD14-FITC (BD Biosciences), CD15-APC (BD Biosciences). For patient samples, additional hCD45-APC-H7 (BD Biosciences), Annexin V-Pacific Blue (BioLegend, San Diego, Calif., USA) and 7-AAD (Sigma) were used; and for bone marrow mice cells, additional CD33-FITC, CD44-PE Cy7, mCD45-PerCP Cy 5.5, CD14-Alexa 700 were used. Data were collected on a LSRII or a LSRFortessa cytometer (BD Biosciences), and analyzed with FlowJo software. A minimum of 10,000 events was collected.

Clonogenic assay. AML cells (106/mL) were grown in duplicate in H4230 methylcellulose medium (Stem Cell Technologies) supplemented with 10% 5637-conditionned medium as described (Récher C et al, Blood 2005). IRC-083864 was added at increasing concentrations in the culture medium. Cells were incubated for 7 days in a humidified CO2 incubator. Leukemic colonies were then scored under an inverted microscope.

Morphological examination. 105 cells were spun at 500 rpm for 5 minutes onto glass slides and May-Grünwald-Giemsa stained at the Toulouse University Hospital hematology laboratory.

In vivo experiments. Animals were used in accordance to a protocol reviewed and approved by the Institutional Animal Care and User Ethical Committee of the UMS006 and Region Midi-Pyrénées (Approval#13-U1037-JES08). NOD/LtSz-scid IL-2Rγchainnull (NSG) mice (Sanchez P V et al) were produced at the Genotoul Anexplo platform in Toulouse (France) using breeders obtained from The Charles River Laboratory. Mice were housed in sterile conditions using HEPA filtered micro-isolators and fed with irradiated food and acidified water. Transplanted mice were treated with antibiotics (enrofloxacin) for the duration of the experiment. Only female mice were considered for this experiment because of higher toxicity of IRC-083864 in males NSG mice in preliminary toxicity assays. Adult mice (6 or 7-week old) were treated with 20 mg/kg Busulfan (Busilvex, Pierre Fabre, France) by i.p. administration 24 hours before injection of leukemic cells. Cultured MOLM-14 cells were washed in PBS and cleared of aggregates and debris using a 0.2 mm cell filter, and suspended in PBS at a final concentration of 2 million cells per 200 µL of PBS per mouse for i.v. injection. IRC-083864 (5 mg/kg/week) was then administrated to leukemic mice by i.p. injection. Daily monitoring of mice for symptoms of disease (ruffled coat, hunched back, weakness and reduced motility) determined the time of animal euthanasia. Cell differentiation was monitored after two IRC-083864 injections: mice were humanely killed in accordance with IACUC protocols. Bone marrow (mixed from tibias and femurs) were dissected, flushed in PBS and made into single cell suspensions for analysis by flow cytometry and cytospins.

Statistics. Experiments in cell lines were performed at least 3 times. Results are expressed as mean value+/−SEM. Statistical analysis of the data was performed by the Mann-Whitney U test and two-way Anova or Kruskal-Wallis test for multiple comparisons using GraphPad Prism software, version 5.0 (GraphPad Software Inc., La Jolla, Calif.). Differences were considered as significant for p values <0.05; *p<0.05, ***p<0.001.

Results

CDC25A is an Early Target Downstream of FLT3-ITD

In order to identify links between the FLT3-ITD mutated receptor and cell cycle progression, we investigated the expression of cell cycle regulating proteins upon FLT3-ITD inhibition in MV4-11 and MOLM-14, two AML cell lines carrying FLT3-ITD mutation. Two unrelated pharmacological inhibitors of FLT3 (FLT3 inhibitor III and the potent new generation inhibitor AC220, quizartinib) induced CDC25A down-regulation in these cell lines (FIG. 1a). Neither the other members of the CDC25 phosphatase family CDC25B and CDC25C, nor the key cell cycle regulators cyclin A, cyclin D1 or p27Kip1 were significantly affected in these conditions (FIG. 1a). Cell cycle distribution of AML cells was not modified after two hours in the presence of FLT3 inhibitor III (not shown), indicating that CDC25A down-regulation was not a consequence of cell cycle arrest. The efficiency of FLT3 inhibitors in FLT3-ITD expressing cell lines was ascertained by the inhibition of Akt, STAT5 and ERK phosphorylation, three major pathways activated downstream of FLT3-ITD. As a confirmation of these data, CDC25A down-regulation also occurred in response to FLT3-ITD inhibition in the murine cell line BaF3 constitutively expressing FLT3-ITD. Importantly, FLT3 inhibitor did not modify CDC25A protein level in FLT3-wild type leukemic cell lines KG1 and HL-60 or in the FLT3 non-expressing cell line K562 (FIG. 1b).

Mechanisms of CDC25A Regulation Downstream of FLT3-ITD

Figure 4A:
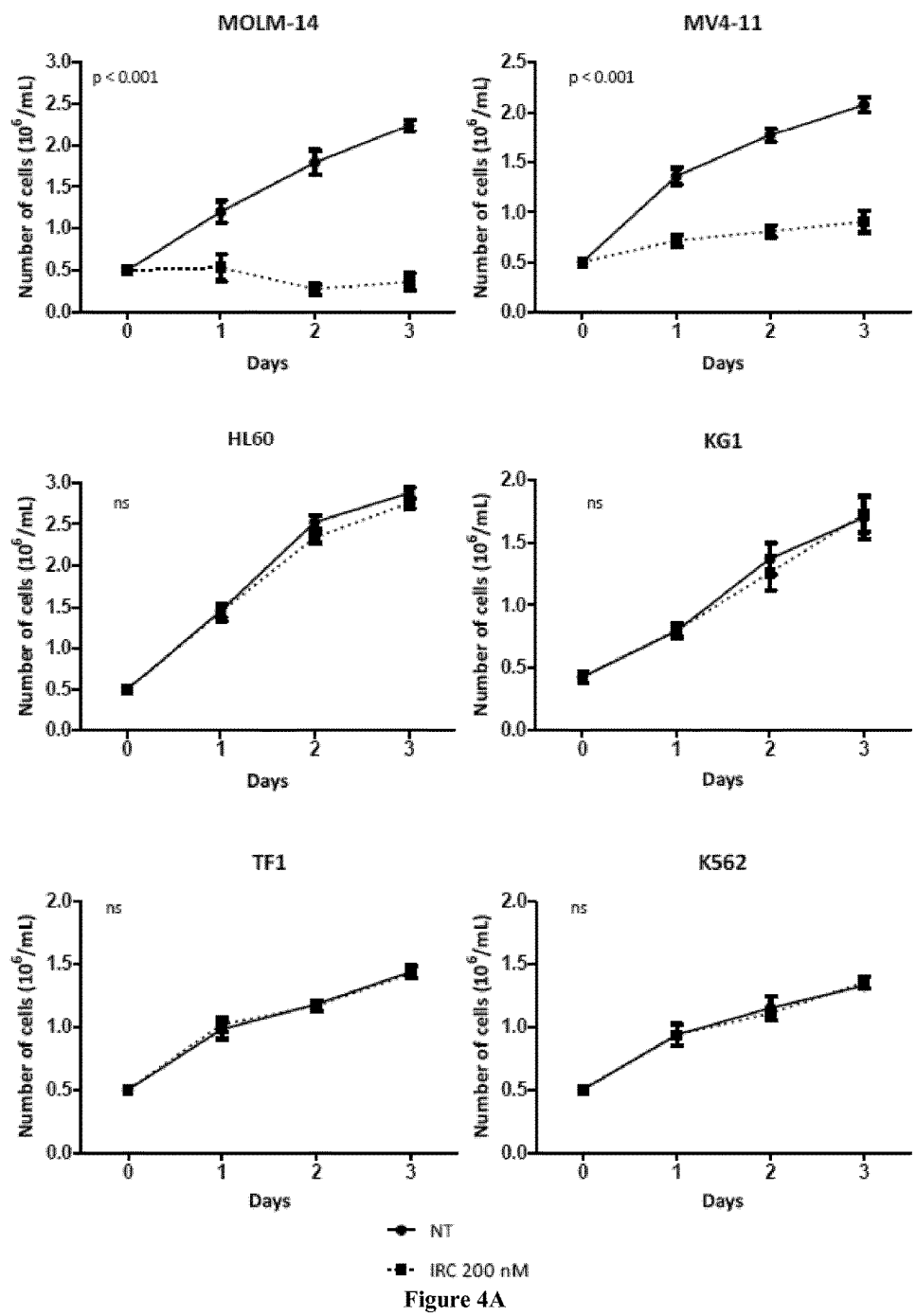
Figure 4B:
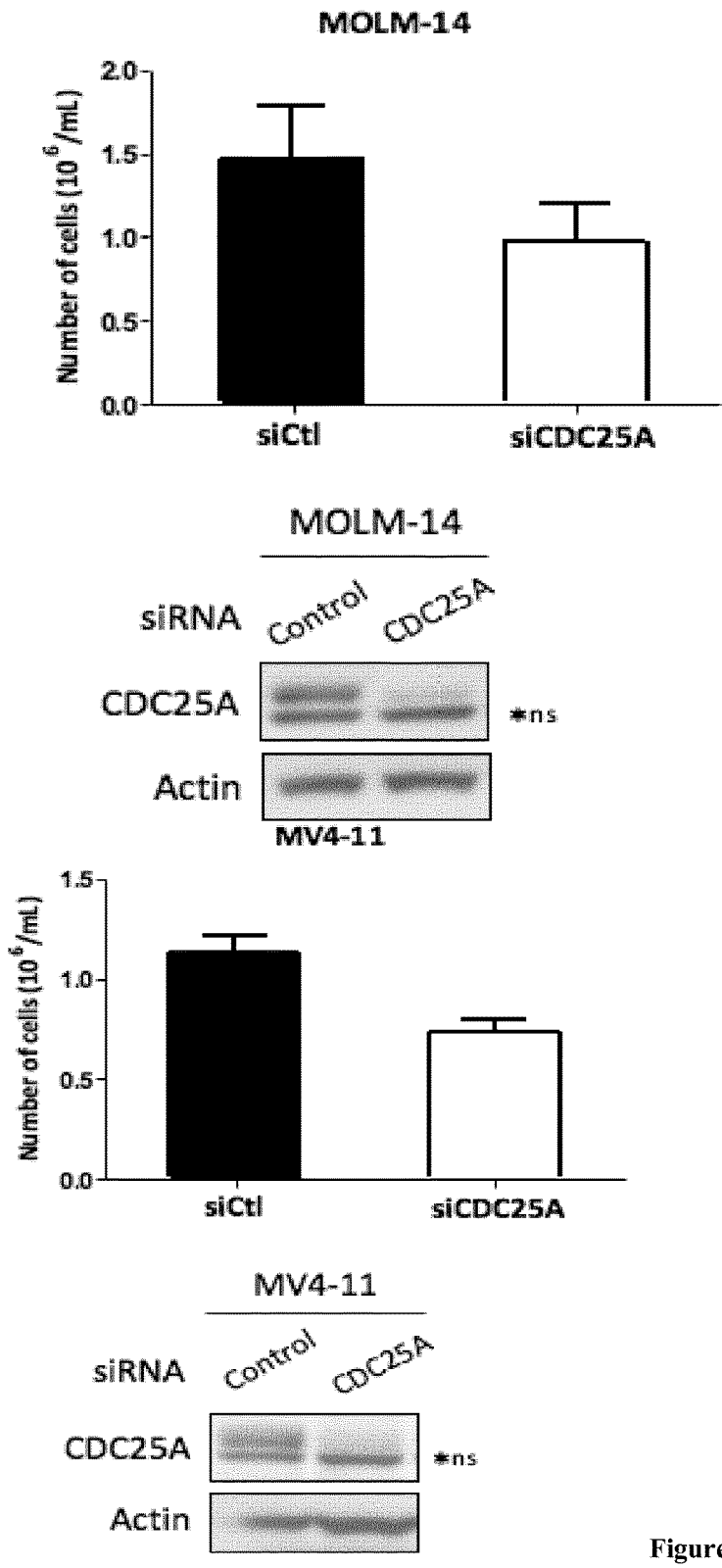

We then asked whether FLT3-ITD cells are dependent on CDC25A activity for their proliferation. First we used IRC-083864, a potent pharmacological inhibitor of CDC25 (A, B and C) previously characterized in vitro and in vivo in different cancer models (Brezak M C et al, Int J Cancer 2009). IRC-083864 induced a robust inhibition of MV4-11 and MOLM-14 cell lines proliferation, but did not decrease the proliferation of KG1, HL-60, TF-1 and K562 control cells (FIG. 4a). In addition, IRC-083864 had no effect on KG1 and HL60 cells proliferation upon stimulation by FLT3 ligand. At concentrations inhibiting cell proliferation, IRC-083864 did not induce either significant cell death, or accumulation in a particular phase of the cell cycle. Since IRC-083864specificity does not allow discrimination between CDC25A, CDC25B or CDC25C, we then performed RNA interference experiments to estimate more specifically the impact of CDC25A on proliferation of FLT3-ITD positive cells. We performed transfections with two independent siRNA against the coding region and the 3'-UTR of CDC25A. As shown in FIG. 4b, RNA interference-mediated CDC25A down-regulation reduced the proliferation of MOLM-14 and MV4-11 cells. Importantly, similar down-regulation of CDC25A had negligible effect on KG1 cells proliferation confirming that FLT3-ITD positive cells are more dependent on CDC25A than FLT3-ITD negative ones.

To verify the involvement of STAT5 in CDC25A regulation, we performed RNA interference experiments, which also induced CDC25A protein down-regulation in MOLM-14 and MV4-11 cells, confirming the results observed with pharmacological inhibition (FIG. 2b).

In order to further precise CDC25A regulation mechanisms, we then asked whether stability or synthesis of the protein were modified in response to FLT3-ITD inhibition. First, we performed time course experiments of CDC25A protein accumulation in response to proteasome inhibition (FIG. 3a). In these conditions, the accumulation of CDC25A was significantly decreased in the presence of FLT3 inhibitors, suggesting that the rate of protein synthesis was dependent on FLT3-ITD activity. Since STAT5 is a transcription factor, we then estimated variations of CDC25A mRNA level by quantitative RT-PCR in response to FLT3-ITD inhibition. As shown in FIG. 3b, inhibiting FLT3-ITD for two hours significantly reduced CDC25A mRNA level in MOLM-14 cells, suggesting that STAT5 could be a transcriptional regulator of CDC25A downstream of FLT3-ITD. Finally, we performed half-life experiments measurements in the presence of cycloheximide (FIG. 3c). The rates of CDC25A down-regulation in the presence of cycloheximide was similar in the presence or the absence of FLT3 inhibitor, establishing that FLT3-ITD inhibition did not significantly modify the stability of CDC25A protein. Altogether, these data suggest that CDC25A is regulated at a transcriptional level downstream of FLT3-ITD, and that STAT5 activity is central for this regulation.

CDC25A is an Important Determinant of FLT3-ITD Cells Proliferation

We then asked whether FLT3-ITD cells are dependent on CDC25A activity for their proliferation. First we used IRC-083864, a potent pharmacological inhibitor of CDC25 (A, B and C) previously characterized in vitro and in vivo in different cancer models (Brezak M C et al, Int J Cancer 2009). IRC-083864 induced a robust inhibition of MV4-11 and MOLM-14 cell lines proliferation, but did not decrease the proliferation of KG1, HL-60, TF-1 and K562 control cells (FIG. 4a). In addition, IRC-083864 had no effect on KG1 and HL60 cells proliferation upon stimulation by FLT3 ligand. At concentrations inhibiting cell proliferation, IRC-083864 did not induce neither significant cell death, nor accumulation in a particular phase of the cell cycle. Since IRC-083864 specificity does not allow to discriminate between CDC25A, CDC25B or CDC25C, we then performed RNA interference experiments to estimate more specifically the impact of CDC25A on proliferation of FLT3-ITD positive cells. We performed transfections with two independent siRNA against the coding region and the 3'-UTR of CDC25A. As shown in FIG. 4b, RNA interference-mediated CDC25A down-regulation reduced the proliferation of MOLM-14 and MV4-11 cells. Importantly, similar down-regulation of CDC25A had negligible effect on KG1 cells proliferation confirming that FLT3-ITD positive cells are more dependent on CDC25A than FLT3-ITD negative ones.

Figure 4C:
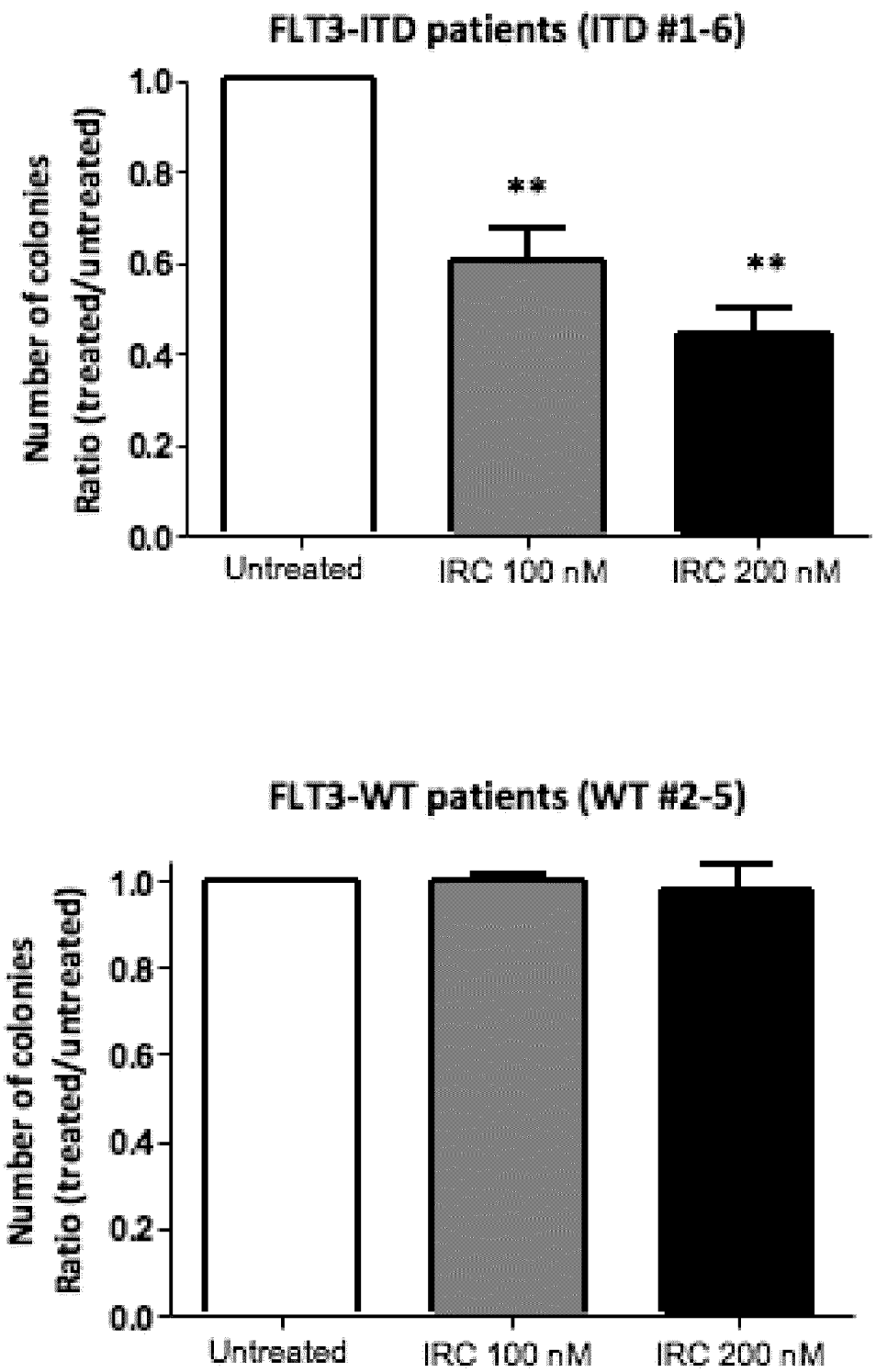

To extend these data, we then measured the impact of CDC25 inhibition on the proliferation of primary AML cells. The main biological characteristics of these samples are depicted in Table 1. The clonogenic potential of FLT3-ITD positive primary cells in semi-solid 5637 conditioned culture medium was significantly reduced in the presence of IRC-083864 in a dose-dependent manner (FIG. 4c, upper panel). By comparison, primary cells from patients expressing wild-type FLT3 (FIG. 4c, lower panel) were not sensitive to CDC25 inhibition in these conditions, confirming the results obtained with established cell lines (FIG. 4a). Similar results were obtained with a semi-solid medium containing recombinant growth factors GM-CSF, FLT3 ligand, and IL-3. Taken together, these data demonstrate that FLT3-ITD expressing cells are highly dependent on CDC25A protein expression and phosphatase activity for their proliferation.

Figure 4D:
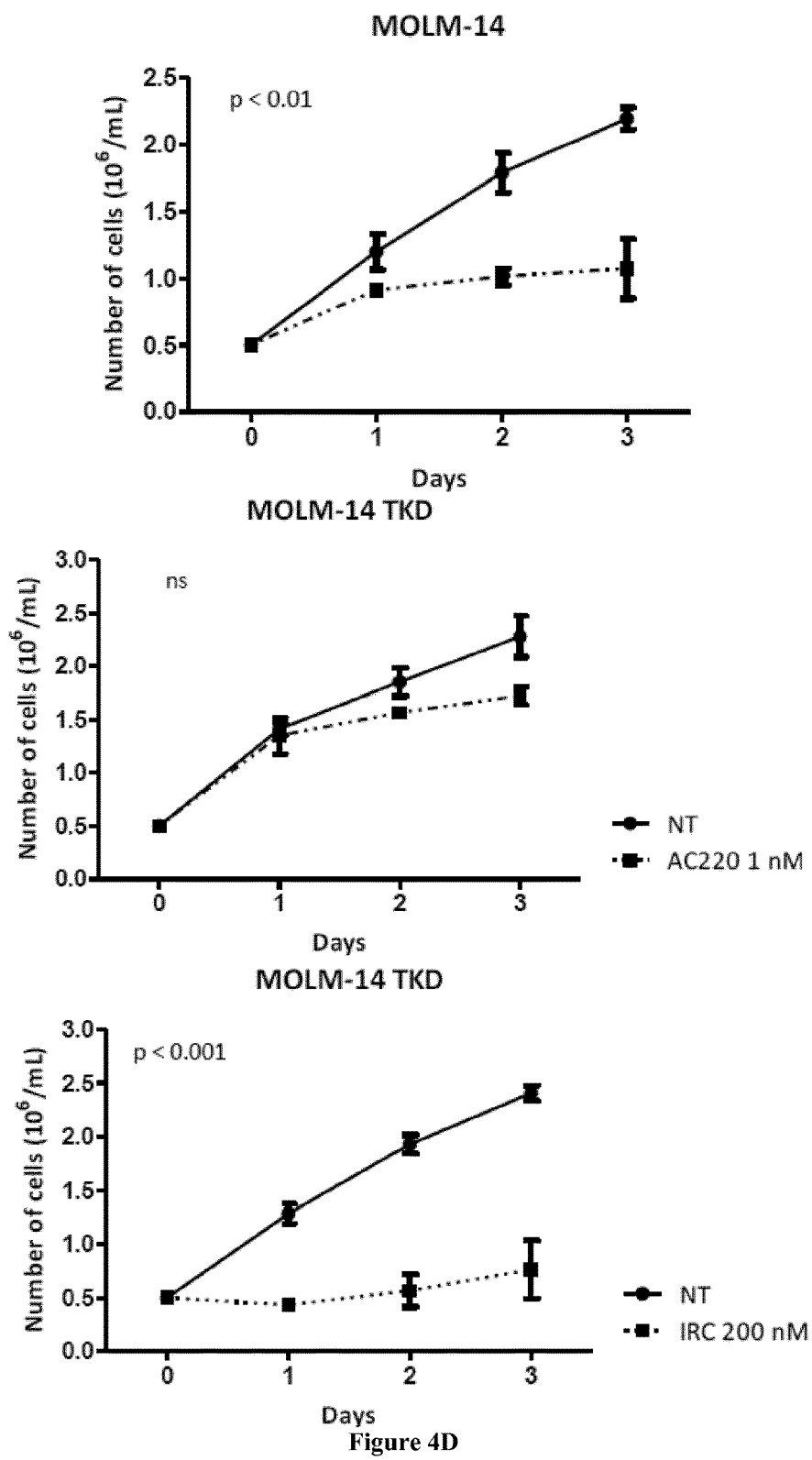

FLT3-ITD/TKD Expressing Cells are Resistant to AC220 but Remain Sensitive to CDC25 Inhibition In recent clinical trials performed with pharmacological FLT3 inhibitors such as quizartinib or sorafenib (Pratz K W et al Curr Drug Targets 2010), heterogeneous mechanisms were suggested to contribute to FLT3 inhibitors resistance, and among them FLT3 kinase domain mutations were the most frequently reported (Alvarado Y et al. Cancer. 2014). We consequently developed a cellular model consisting of MOLM-14 cells transfected with a FLT3-ITD mutant with a D835Y amino-acid substitution within the FLT3 kinase domain (FLT3-ITD-D835Y; FLT3-ITD/TKD). In MOLM-14 and in MOLM-14 expressing FLT3-ITD/TKD, treatment with 1 nM AC220 induced low levels of cell death (not shown), and as expected, ITD/TKD cells were resistant to AC220 by comparison with parental MOLM-14 (FIG. 4D; upper panel). By contrast, 200 nM IRC-083864 induced cell proliferation arrest and cell death similar to that observed with MOLM-14 and MV4-11 cell lines (FIG. 4D; lower panel), suggesting that in some circumstances CDC25 inhibition could overcome resistance to FLT3 inhibitors.

CDC25A Level Predicts Clonogenic Capacity of FLT3-ITD Primary Cells

We then investigated the expression level of CDC25A mRNA in a cohort of 188 non promyelocytic AML young patients (aged 18-65) treated by intensive chemotherapy in Toulouse University Hospital in the 2000-2010 period. CDC25A mRNA expression was divided into low expression and high expression according to the median value of the entire cohort. We observed no difference in the expression of CDC25A between FLT3-wt and FLT3-ITD patients. FLT3-ITD allelic ratio or insertion length were also not determinants for CDC25A expression. Since CDC25A appears as an important actor of cell proliferation in FLT3-ITD cells (see FIG. 4), we looked for correlations between CDC25A expression and clonogenic potential in FLT3-ITD patients. Clonogenic assays were performed at diagnosis for 151 patients. We first restricted our analysis to the intermediate 204 risk cytogenetic group (n=100) where FLT3-ITD has its prognostic significance. As shown in Table 2, high CDC25A mRNA levels nicely correlate with higher clonogenic potential in FLT3-ITD patients, while this is not the case in FLT3-wt ones. Similar results were obtained in the normal karyotype subgroup (n=67). These data suggest that high CDC25A expression confers proliferation advantage to FLT3-ITD positive cells.

CDC25A is Involved in FLT3-ITD AML Cells Differentiation Arrest

Figure 5A:
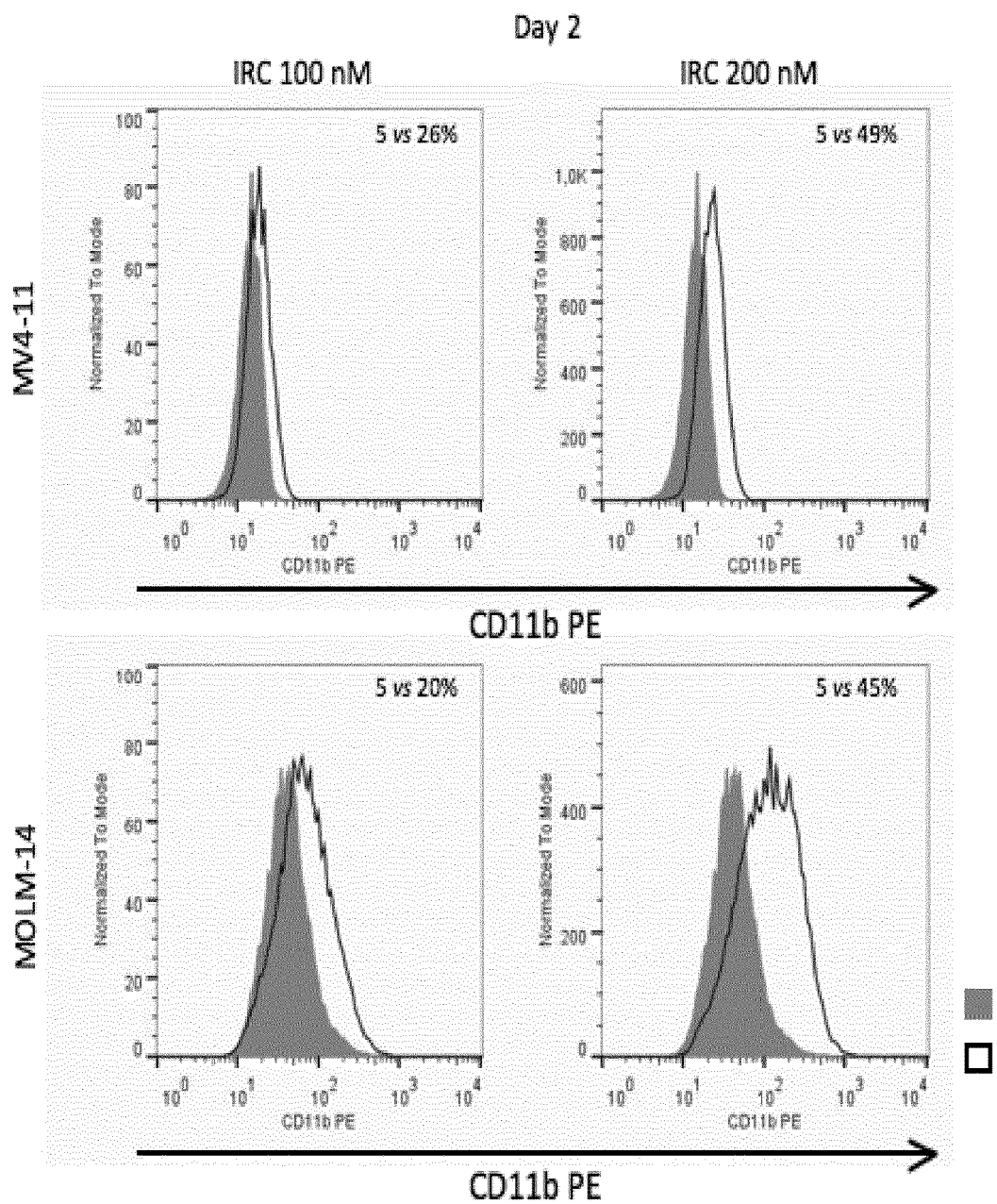
Figure 5B:
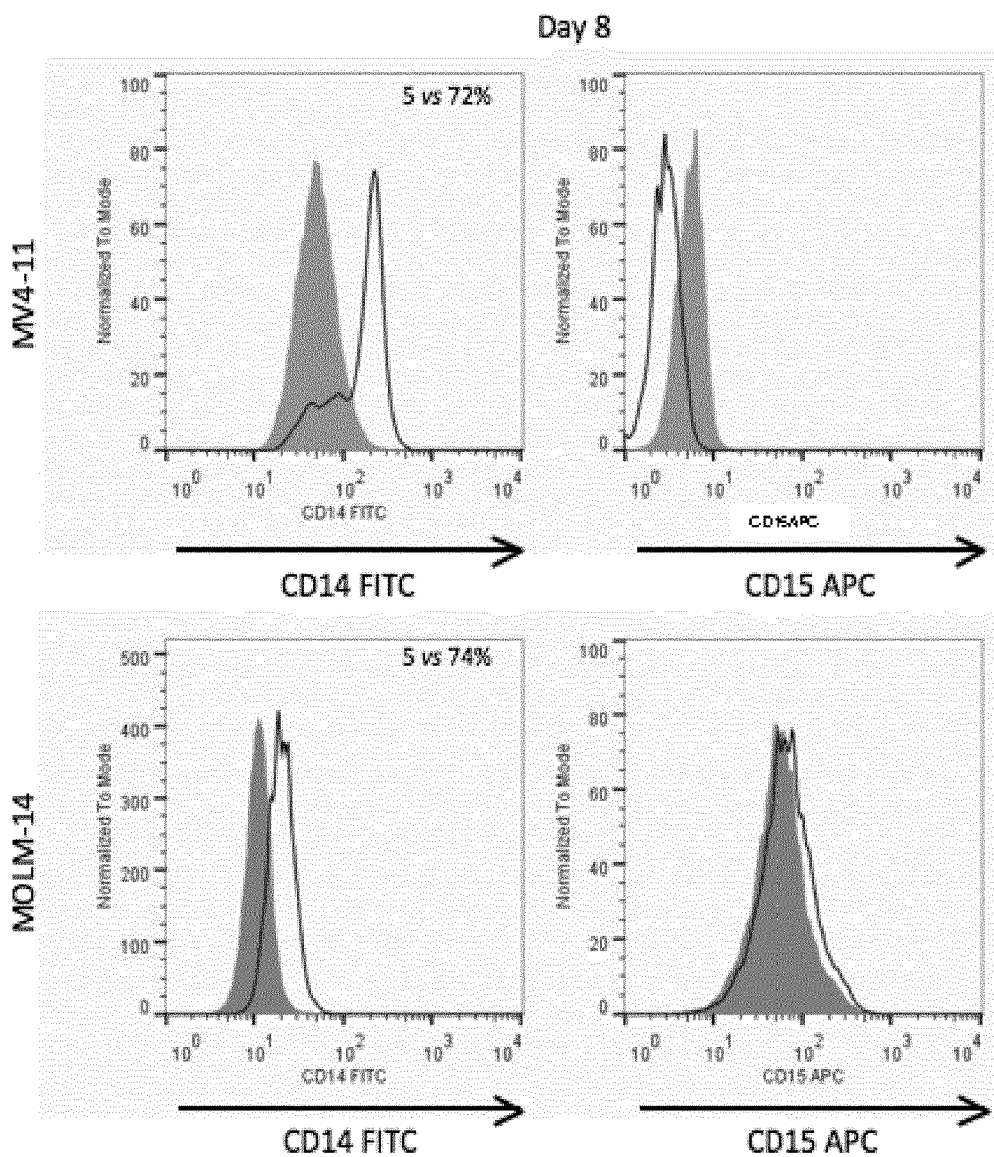

Involvement of the cyclin-dependent kinase CDK1 in FLT3-ITD positive cells differentiation arrest was recently reported (Radomska H S et al, JCI 2012). Since CDK1 is a major substrate of CDC25 phosphatases during mitosis, we reasoned that CDC25A could be a master regulator of leukemic cells differentiation through its CDK1 activating function. To test this hypothesis, MV4-11 and MOLM-14 cells were treated with IRC-083864, and the differentiation state of the cells was followed by cell surface markers expression and by morphological examination at different times. As shown in FIG. 5a, expression of the early granulo-monocytic marker CD11b was induced in a dose dependent manner as early as two days after CDC25 inhibition. After 8 days of treatment, the monocytic marker CD14 was increased in both cell lines (FIG. 5b) while CD15 either decreased or did not change significantly at that time. These data suggest that CDC25 inhibition relieves the differentiation block and drives a monocytic differentiation process in FLT3-ITD expressing cell lines. Morphological analyses showed monocytic-like nuclear changes in cells treated with IRC-083864 for 8 and 13 days (FIG. 5c), consistent with cell surface markers expression modifications. In good agreement, IRC-083864 induced also dephosphorylation of C/EBPα on serine 21, a phosphorylation catalyzed by CDK1 and/or ERK and involved in the differentiation arrest of these cells (FIG. 5d). CDC25 inhibition also induced c-myc down-regulation at day 1 and C/EBPε up-regulation at day 6, two additional markers of myeloid differentiation. As a confirmation of these data, modifications of CD11b, CD14 and CD15 markers expression as well as nuclear morphological changes were also observed with another CDC25 inhibitor, NSC-95397.

Figure 5E:
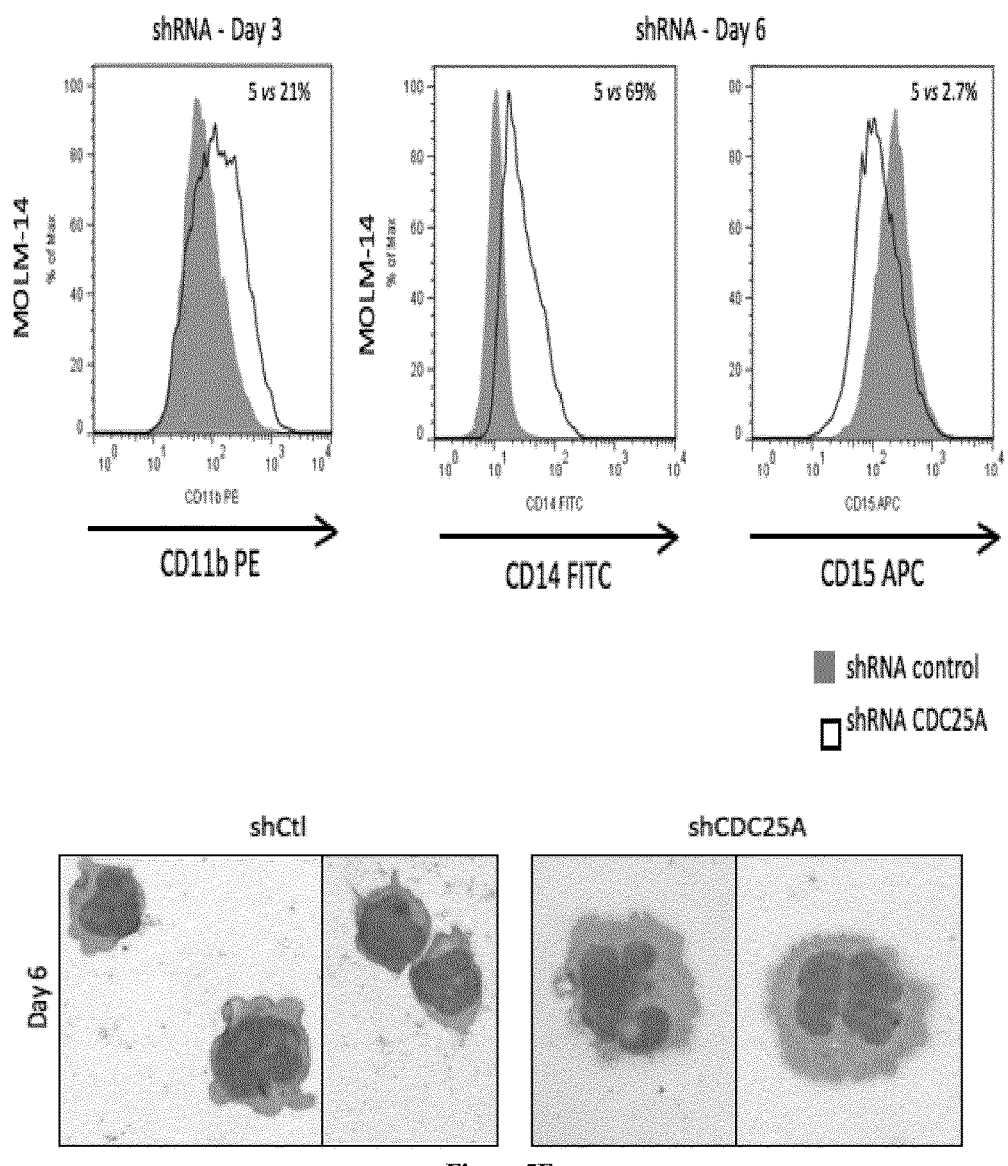
Figure 5F:
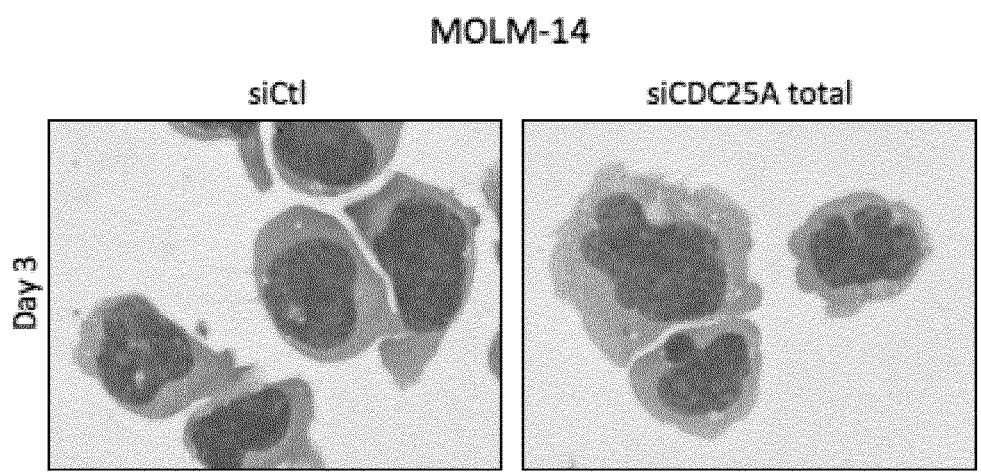
Figure 5F:
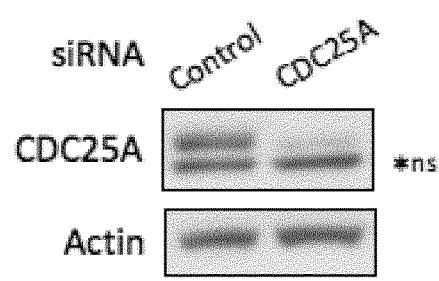

In order to further confirm the role of CDC25A in this differentiation arrest, we performed RNA interference mediated down-regulation of the protein. First, we used lentiviral infection to perform shRNA-mediated CDC25A down-regulation in MOLM-14 cells. As shown in FIG. 5e, down-regulation of CDC25A in these conditions induced CD11b and CD14 expression 3 and 6 days after infection respectively, while CD15 expression decreased, confirming the data obtained with pharmacological inhibition and further arguing for the implication of this phosphatase in the differentiation process. Nuclear modifications were observed at day 6 in morphological analyses. siRNA-mediated CDC25A down-regulation also led to nuclear morphologic modifications at day 3 in MOLM-14 cells (FIG. 5f).

Figure 6A:
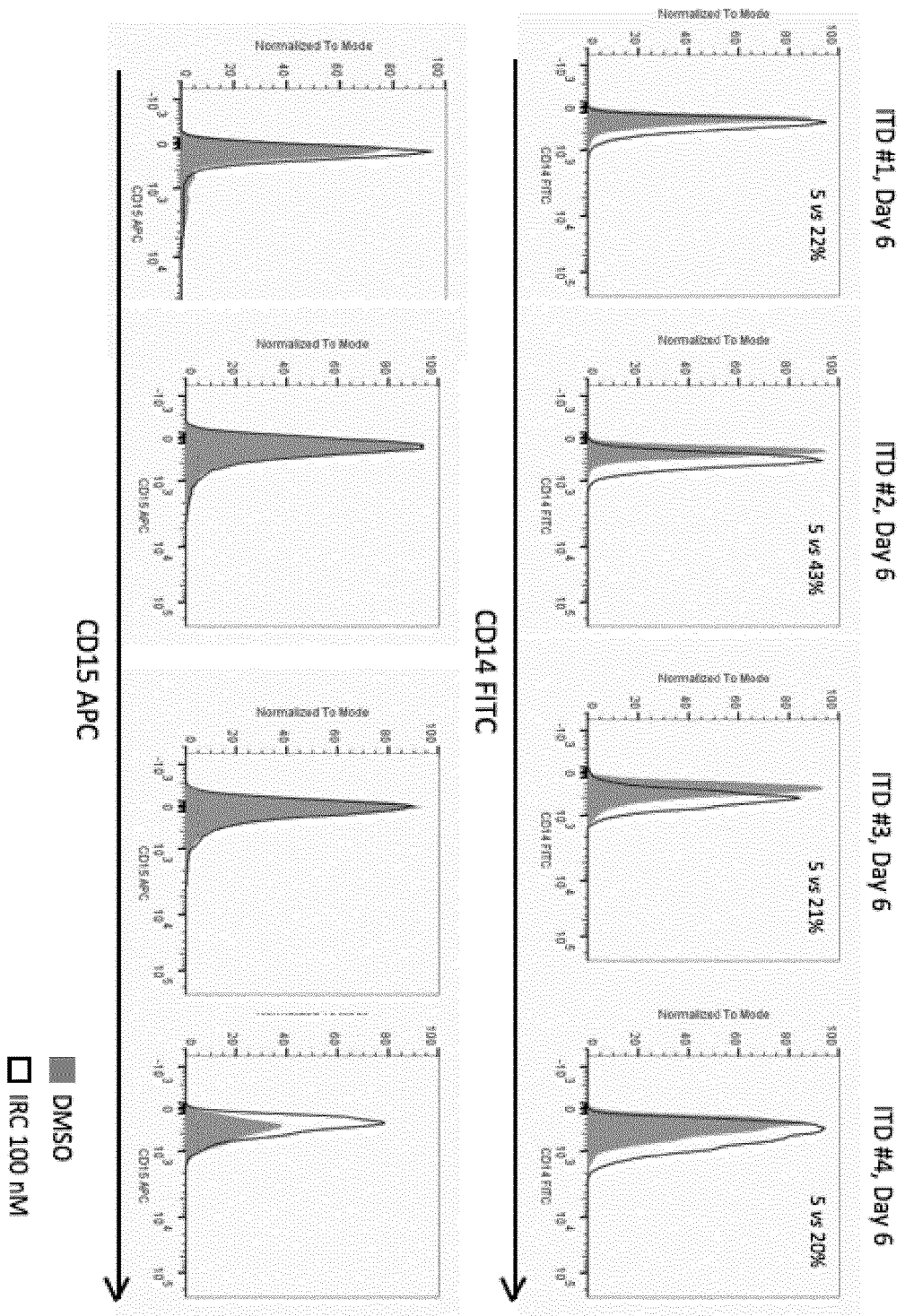

We then asked whether CDC25 inhibition could induce differentiation of primary AML samples expressing either FLT3-ITD or wild-type FLT3. As shown in FIGS. 6a and b, the monocytic-specific differentiation marker CD14 increased while CD15 expression was not modified after 6 days of treatment of FLT3-ITD primary cells with IRC-083864. Consistently, monocytic-like morphological nuclear changes were observed at days 6 and 9 of CDC25 inhibition in these FLT3-ITD expressing cells (FIG. 6c). Similar results were obtained after treatment with the other CDC25 inhibitor NSC-95397, while no evidence of differentiation was observed in FLT3-wild type samples in the same conditions.

CDC25 Inhibition Induces FLT3-ITD AML Cells Differentiation In Vivo

Figure 7C:
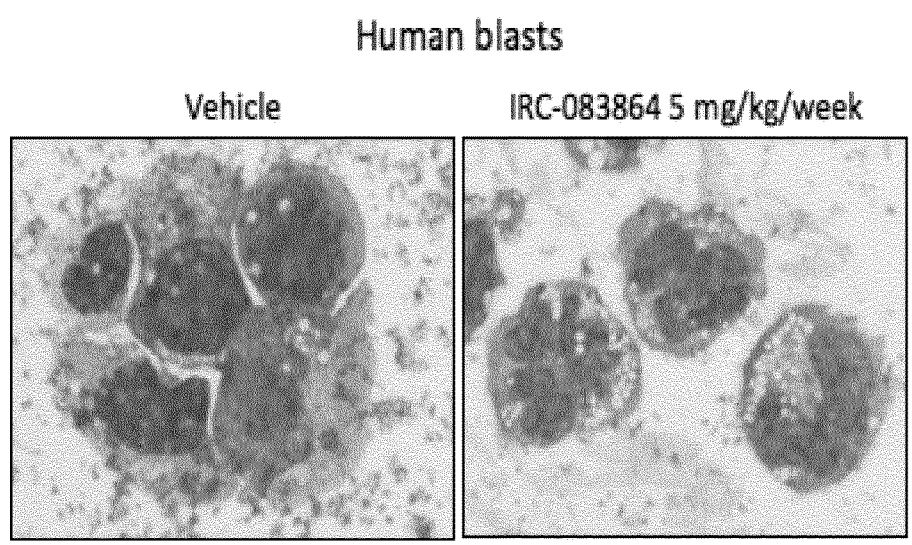

In order to establish if CDC25 inhibition could also drive monocytic differentiation in vivo, we used the NSG mice model of xenograft. NSG mice were injected with 2 millions of MOLM-14 cells after busulfan injection, and then treated with IRC-083864 at 5 mg/kg/week by intra-peritoneal administration. Mice were dissected after two weeks of treatment, and human myeloid cells present in the bone marrow were analyzed for the expression of CD11b, CD14 and CD15 surface proteins. At this time point, no change of CD11b expression could be observed, but as shown in FIGS. 7a and b, MOLM-14 cells from mice treated with IRC-083864 presented increased expression of CD14 and unchanged expression of CD15, nicely reproducing the results obtained in vitro. Morphological analyses of cytospun human bone marrow cells showed monocytic-like nuclear changes in treated mice (FIG. 7c). In these conditions, survival of treated and untreated mice was not different.

Altogether these data demonstrate that inhibiting CDC25A reduces proliferation and induces monocytic differentiation of FLT3-ITD-positive AML cells in vitro and in vivo, and they argue for a central function of this phosphatase in the hematopoietic differentiation arrest of these cells.

Discussion

Because of high frequency and poor prognosis of FLT3-ITD mutation, improving the knowledge of this AML subgroup pathophysiology appears as an essential task for the next years. Major signaling pathways activated by FLT3-ITD have been identified, but downstream effectors, as well as their respective involvements in cell proliferation and drug resistance remain to be specified. Large phosphoproteomic analysis performed in FLT3-ITD expressing cells identified a panel of potential downstream targets of Pim and Akt, two well recognized players of FLT3-ITD oncogenic potential (Choudhary C et al, Mol Cell 2009), but functional importance of these proteins in FLT3-ITD AML remained elusive. In this work, we demonstrate that the dual specificity phosphatase CDC25A, a major activator of cyclin-dependent kinases during different phases of the cell cycle, is regulated very early downstream of FLT3-ITD. Our data argue for a STAT5-dependent transcriptional mechanism being at the origin of this regulation, but we cannot rule out that CDC25A protein level is also governed at the translational level, as we recently observed down-stream of JAK2 V617F, another oncogenic tyrosine kinase involved in myeloproliferative disease (Gautier E F et al, Blood 2012). Transcriptional regulation of CDC25A by STAT5 has not been reported up to now, but the involvement of STAT3 in both negative and positive transcriptional regulation of CDC25A has been described (Barré B et al, JBC 2005). Different studies recognized the importance of STAT5 in FLT3-ITD signaling and leukemic cells transformation (Hayakawa F et al, Mizuki M et al, Spiekermann K et al), and targeting of this pathway constitutes an important axis of therapeutic research (Nelson E A et al). Interestingly, we recently demonstrated that the STAT5/Pim signaling pathway also governs FLT3-ITD positive AML cells resistance and proliferation through direct phosphorylation of CHK1 ser/thr kinase on Ser 280 by Pim (Yuan L L et al, Leukemia 2014). Further experiments are needed to better understand CDC25A regulation by STAT transcription factors in AML cells.

In this work, we highlighted a central role for CDC25A, a major regulator of cell cycle progression, in the differentiation processes of FLT3-ITD AML subtype. Abnormalities of transcription factors-induced differentiation are observed in one third of AML (PML-RARA, AML1-ETO, CBFβ and C/EBPα). In particular, mutations in the C/EBPα gene are detected in 10% of these pathologies, and C/EBPα plays a key role in normal granulocytic or monocytic differentiation, depending on its dimerization partner (Paz-Priel I et al, Crit Rev Oncog 2011). Differentiation arrest in FLT3-ITD AML was recently described to be dependent on the phosphorylation of C/EBPα on serine 21 by the ERK kinase and/or the mitotic cyclin dependent kinase CDK1/cyclin B1 (Radomska H S et al, JCI 2012). These authors proposed FLT3-ITD-dependent regulation of cyclin B1 protein as a key parameter of CDK1 activity, and consequent C/EBP□□ phosphorylation and differentiation arrest in this model. Our work suggests that CDC25A, in addition to cyclin B1, is another key regulator of CDK1 activity downstream of FLT3-ITD. This would suggest that FLT3-ITD up-regulates CDK1 activity by different ways, both by CDC25A-dependent dephosphorylation of Thr14/Tyr15, and by accumulation of cyclin B1 and its subsequent association with CDK1. The molecular mechanism of cyclin B1 accumulation in this context, and whether CDC25A activity could be involved in this process, remain to be established. CDC25A is involved in different phases of the cell cycle, and to this respect, is considered as regulator of different CDKs. Its role as an activator of CDK2 and the G1/S transition and during DNA replication is well established, and its action on the G1 CDK4/CDK6-cyclin D1 complex has been recently highlighted (Bertero T et al, CDD 2013). Our data do not allow to distinguish which CDKs are regulated by CDC25A and involved in the differentiation process downstream of FLT3-ITD. In consequence, we cannot exclude that CDK2, and/or CDK4/CDK6 are important actors of this process. This hypothesis would be in line with the very recent identification of CDK6 as a critical effector of MLL fusions in leukemogenesis, underscoring that cell cycle regulators may have distinct, non-canonical, and non-redundant functions in different contexts (Placke T et al, Blood 2014). By acting on different CDK/cyclin complexes, CDC25 inhibitors would constitute interesting candidates to increase the therapeutic tools in the AML personalized treatment, and intense research is ongoing to give rise to new potent compounds (Song Y et al, Eur J Med Chem 2014).

Since a few works reported the possible importance of CDC25C (Caduil J S et al, Leuk. Lymphoma 2008) and CDC25B (Reikvam H et al, J. Hematol 2014) in AML, CDC25 family members inhibition in these pathologies may be of interest in the future (Brenner A K et al, Molecules 2014). From a more general point of view, the ability of cells to escape terminal differentiation is one of the characteristics of cancer (Hanahan D et al, Cell 2000), and AML represents a paradigm for this phenomenon (Tenen D G et al, Nat Rev Cancer 2003). Reinducing leukemic cells differentiation constitutes an important alternative to genotoxic therapeutic agents currently used to treat these pathologies, but up to now, this approach is only routinely used in the case of promyelocytic leukemia with all-transretinoic acid or arsenic trioxide, which transformed the prognosis of this disease. In the non-promyelocytic leukemia, the discovery of key mutations this last decade led to intense efforts to improve therapeutic strategies (Schlenk R F et al, Patel J P et al NEJM 2012, Patel J P, ASH Edu 2012). In parallel, in AML characterized by mutation of the IDH2 gene, preliminary results of a phase I assay of the IDH2 inhibitor AG-221 showed encouraging rates of response, and nice differentiation of treated leukemic cells in vitro and clinically with cases of differentiation syndrome (Agresta S et al, EHA 2014). FLT3 inhibition is one of the major promising targeted therapies in this subset. To date, one of the most potent and clinically advanced molecule is AC220 (quizartinib) (Wander S A et al, Ther Adv Hematol 2014 Cortes J E et al, Blood 2012; Levis M J et al, Blood 2012 and Kampa-Schittenhelm K M et al, Mol Cancer 2013), and relief of differentiation block in vitro and clinically (Sexauer A et al, Blood 2012) is one of the interesting mechanism of action described for this drug. This pro-differentiation effect of FLT3 inhibition seems to be an on-target effect, as the in vitro results were obtained with other FLT3 inhibitors (sorafenib, lestaurtinib and tandutinib) (Sexauer A et al, Blood 2012; Zheng R et al, Blood 2004 and Radomska H S et al, J Exp Med 2006). These recent observations appeared somehow controversial, since transgenic mice models expressing FLT3-ITD developed myeloproliferative neoplasms rather than AML, suggesting that FLT3-ITD expression by itself did not significantly affect the hematopoietic differentiation process in vivo (Li L et al, Blood 2008).

Better understanding of signaling and cell cycle molecules impacting hematopoietic differentiation downstream of FLT3-ITD will probably give some keys for future treatments of this AML subtype.

TABLE 1

Figure 6B:
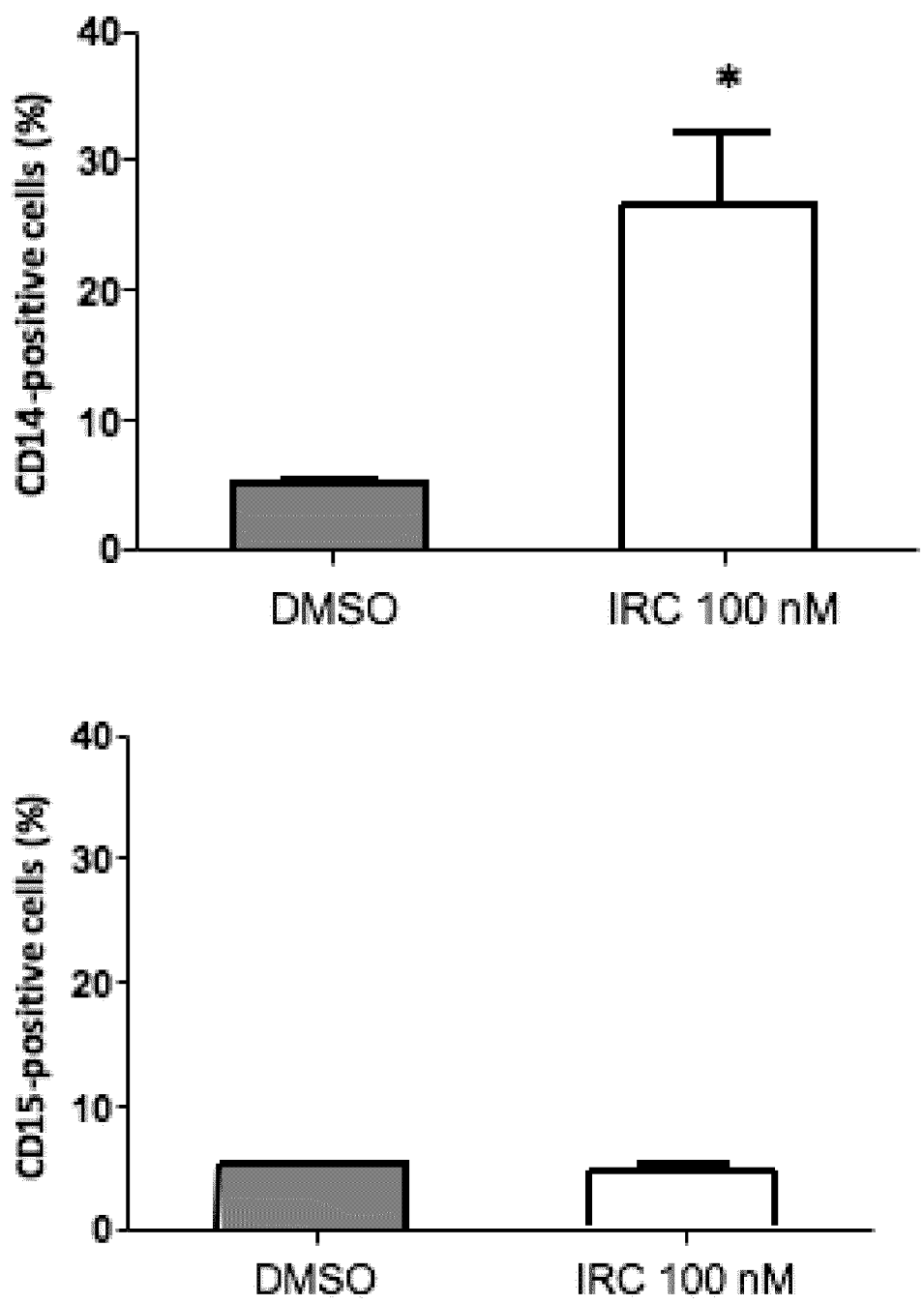
Figure 6C:
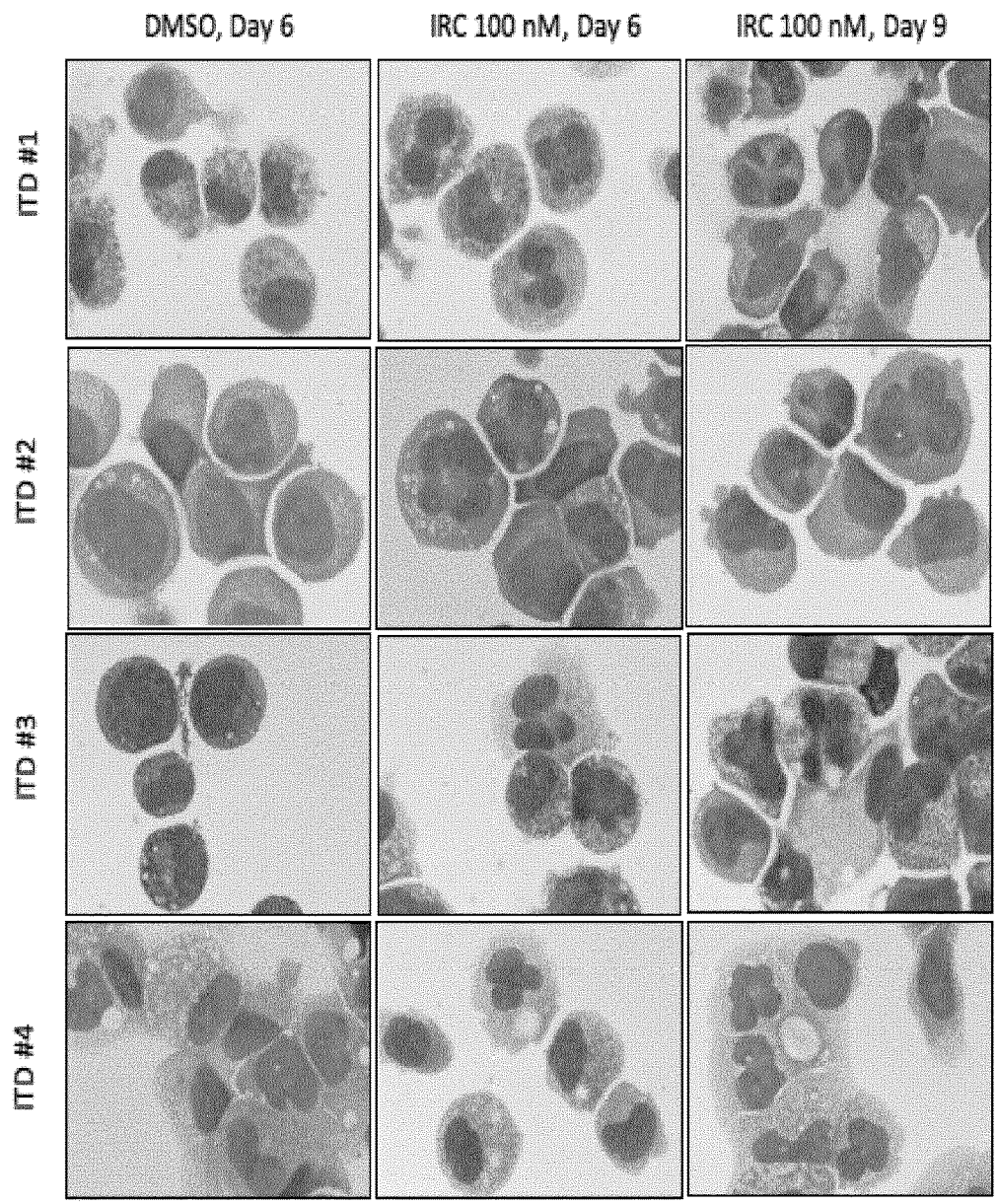

Biological properties of primary AML samples
A summary of the main biological properties of primary AML samples used in FIG. 4d and FIG. 6. French-American-British (FAB) classification, karyotype, as well as FLT3-ITD (with allelic ratio when mutated) and NPM1 mutational status are listed.

| Sample | FAB | Karyotype | FLT3 | NPM1 |
|---|---|---|---|---|
| ITD #1 | 5 | Normal | ITD 30% | NPM1c |
| ITD #2 | NA | Normal | ITD 27% | NPM1c |
| ITD #3 | 4 | Normal | ITD 45% | WT |
| ITD #4 | 2 | t (6;9) | ITD 18% | WT |
| ITD #5 | 2 | t (6;9) | ITD 69% | WT |
| ITD #6 | 1 | Normal | ITD 24% | WT |
| WT #1 | 1 | del (7p) | WT | WT |
| WT #2 | 1 | Normal | WT | NPM1c |
| WT #3 | 2 | Normal | WT | NPM1c |
| WT #4 | 2 | Normal | WT | WT |
| WT #5 | 1 | Normal | WT | NPM1c |

NA: non available;
WT: wild-type;
NPM1c: NPM1 cytoplasmic, ie. mutated

TABLE 2

Table 2: Clonogenic properties of AMI cells according to CDC25A mRNA expression

|  | Low CDC25A median (IQR) | High CDCZSA median (IQR) | p* |
|---|---|---|---|
| Total intermediate karyotype (n = 100) | 850 (0-7850) | 2400 (150-10800) | 0.16 |
| Intermediate karyotype with FLT3-ITD (n = 35) | 200 (0-1240) | 5575 (2200-17850) | 0.03 |
| Intermediate karyotype with FLT3-WT (n = 59) | 2225 (0-11650) | 1100 (100-10800) | 0.76 |
| Normal karyotype with FLT3-ITD (n = 31) | 650 (0-4650) | 5250 (1975-12638) | 0.09 |
| Normal karyotype with FLT3-WT (n = 36) | 2550 (0-8050) | 3800 (250-11850) | 0.45 |

Values are expressed in number of clones per $10^6$ cells.
*Comparisons between low CDC25A and high CDC25A subgroups were performed using Mann-Whitney U test

REFERENCES

Throughout this application, various references describe the state of the art to which this invention pertains. The disclosures of these references are hereby incorporated by reference into the present disclosure.

Meyer S C, Levine R L. Translational implications of somatic genomics in acute myeloid leukaemia. Lancet Oncol. 2014 August; 15(9):e382-e394

Nakao M, Yokota S, Iwai T, Kaneko H, Horiike S, Kashima K, Sonoda Y, Fujimoto T, Misawa S. Internal tandem duplication of the flt3 gene found in acute myeloid leukemia. Leukemia. 1996 December; 10(12): 1911-8

Thiede C, Steudel C, Mohr B, Schaich M, Schäkel U, Platzbecker U, Wermke M, Bornhäuser M, Ritter M, Neubauer A, Ehninger G, Illmer T. Analysis of FLT3-activating mutations in 979 patients with acute myelogenous leukemia: association with FAB subtypes and identification of subgroups with poor prognosis. Blood. 2002 Jun. 15; 99(12):4326-35

Döhner H, Estey E H, Amadori S, Appelbaum F R, Büchner T, Burnett A K, Dombret H, Fenaux P, Grimwade D, Larson R A, Lo-Coco F, Naoe T, Niederwieser D, Ossenkoppele G J, Sanz M A, Sierra J, Tallman M S, Löwenberg B, Bloomfield C D; European LeukemiaNet. Diagnosis and management of acute myeloid leukemia in adults: recommendations from an international expert panel, on behalf of the European LeukemiaNet. Blood. 2010 Jan. 21; 115(3):453-74

Böiers C, Buza-Vidas N, Jensen C T, Pronk C J, Kharazi S, Wittmann L, Sitnicka E, Hultquist A, Jacobsen S E. Expression and role of FLT3 in regulation of the earliest stage of normal granulocyte-monocyte progenitor development. Blood. 2010 Jun. 17; 115(24):5061-8

Levis M, Small D. FLT3: ITDoes matter in leukemia. Leukemia. 2003 September; 17(9): 1738-52

Wander S A, Levis M J, Fathi A T. The evolving role of FLT3 inhibitors in acute myeloid leukemia: quizartinib and beyond. Ther Adv Hematol. 2014 June; 5(3):65-77

Stone R M, Fischer T, Paquette R, Schiller G, Schiffer C A, Ehninger G, Cortes J, Kantarjian H M, DeAngelo D J, Huntsman-Labed A, Dutreix C, del Corral A, Giles F. Phase IB study of the FLT3 kinase inhibitor midostaurin with chemotherapy in younger newly diagnosed adult patients with acute myeloid leukemia. Leukemia. 2012 September; 26(9):2061-8

Serve H, Krug U, Wagner R, Sauerland M C, Heinecke A, Brunnberg U, Schaich M, Ottmann O, Duyster J, Wandt H, Fischer T, Giagounidis A, Neubauer A, Reichle A, Aulitzky W, Noppeney R, Blau I, Kunzmann V, Stuhlmann R, Krämer A, Kreuzer K A, Brandts C, Steffen B, Thiede C, Müller-Tidow C, Ehninger G, Berdel W E. Sorafenib in combination with intensive chemotherapy in elderly patients with acute myeloid leukemia: results from a randomized, placebo-controlled trial. J Clin Oncol. 2013 Sep. 1; 31(25):3110-8

Cortes J E, Perl A E, Dombret H, Kayser S, Steffen B, Rousselot P, Martinelli G, Estey E H, Burnett A K, Gammon G, Trone D, Levis M J. Final Results of a Phase 2 Open-Label, Monotherapy Efficacy and Safety Study of Quizartinib (AC220) in Patients ≥60 Years of Age with FLT3 ITD Positive or Negative Relapsed/Refractory Acute Myeloid Leukemia. Blood (ASH Annual Meeting Abstracts), November 2012; 120: 48.

Levis M J, Perl A E, Dombret H, Döhner H, Steffen B, Rousselot P, Martinelli G, Estey E H, Burnett A K, Gammon G, Trone D, Leo E, Cortes J E. Final Results of a Phase 2 Open-Label, Monotherapy Efficacy and Safety Study of Quizartinib (AC220) in Patients with FLT3-ITD Positive or Negative Relapsed/Refractory Acute Myeloid Leukemia After Second-Line Chemotherapy or Hematopoietic Stem Cell Transplantation. Blood (ASH Annual Meeting Abstracts), November 2012; 120: 673.

Kampa-Schittenhelm K M, Heinrich M C, Akmut F, Döhner H, Döhner K, Schittenhelm M M. Quizartinib (AC220) is a potent second generation class III tyrosine kinase inhibitor that displays a distinct inhibition profile against mutant-FLT3, -PDGFRA and -KIT isoforms. Mol Cancer. 2013 Mar. 7; 12:19

Sexauer A, Perl A, Yang X, Borowitz M, Gocke C, Rajkhowa T, Thiede C, Frattini M, Nybakken G E, Pratz K, Karp J, Smith B D, Levis M. Terminal myeloid differentiation in vivo is induced by FLT3 inhibition in FLT3/ITD AML. Blood. 2012 Nov. 15; 120(20):4205-14

Zheng R, Friedman A D, Levis M, Li L, Weir E G, Small D. Internal tandem duplication mutation of FLT3 blocks myeloid differentiation through suppression of C/EBPalpha expression. Blood. 2004 Mar. 1; 103(5): 1883-90

Radomska H S, Bassères D S, Zheng R, Zhang P, Dayaram T, Yamamoto Y, Sternberg D W, Lokker N, Giese N A, Bohlander S K, Schnittger S, Delmotte M H, Davis R J, Small D, Hiddemann W, Gilliland D G, Tenen D G. Block of C/EBP alpha function by phosphorylation in acute myeloid leukemia with FLT3 activating mutations. J Exp Med. 2006 Feb. 20; 203(2): 371-81

Radomska H S, Alberich-Jordà M, Will B, Gonzalez D, Delwel R, Tenen D G. Targeting CDK1 promotes FLT3-activated acute myeloid leukemia differentiation through C/EBPα. J Clin Invest. 2012 Aug. 1; 122(8): 2955-66

Fernandez-Vidal A, Mazars A, Manenti S. CDC25A: a rebel within the CDC25 phosphatases family? Anticancer Agents Med Chem. 2008 December; 8(8):825-31

Ray D, Kiyokawa H. CDC25A phosphatase: a rate-limiting oncogene that determines genomic stability. Cancer Res. 2008 Mar. 1; 68(5):1251-3

Boutros R, Lobjois V, Ducommun B. CDC25 phosphatases in cancer cells: key players? Good targets? Nat Rev Cancer. 2007 July; 7(7):495-507

Fernandez-Vidal A, Ysebaert L, Didier C, Betous R, De Toni F, Prade-Houdellier N, Demur C, Contour-Galcéra M O, Prévost G P, Ducommun B, Payrastre B, Racaud-Sultan C, Manenti S. Cell adhesion regulates CDC25A expression and proliferation in acute myeloid leukemia. Cancer Res. 2006 Jul. 15; 66(14):7128-35

Fernandez-Vidal A, Mazars A, Gautier E F, Prévost G, Payrastre B, Manenti S. Upregulation of the CDC25A phosphatase down-stream of the NPM/ALK oncogene participates to anaplastic large cell lymphoma enhanced proliferation. Cell Cycle. 2009 May 1; 8(9): 1373-9

Gautier E F, Picard M, Laurent C, Marty C, Villeval J L, Demur C, Delhommeau F, Hexner E, Giraudier S, Bonnevialle N, Ducommun B, Récher C, Laurent G, Manenti S, Mansat-De Mas V. The cell cycle regulator CDC25A is a target for JAK2V617F oncogene. Blood. 2012 Feb. 2; 119(5):1190-9

Brezak M C, Valette A, Quaranta M, Contour-Galcera M O, Jullien D, Lavergne O, Frongia C, Bigg D, Kasprzyk P G, Prevost G P, Ducommun B. IRC-083864, a novel bis quinone inhibitor of CDC25 phosphatases active against human cancer cells. Int J Cancer. 2009 Mar. 15; 124(6):1449-56

Pratz K W and Levis M J. Bench to bedside targeting of FLT3 in acute leukemia. Curr Drug Targets 2010; 11: 781-9

Alvarado Y, Kantarjian H M, Luthra R, Ravandi F, Borthakur G, Garcia-Manero G, Konopleva M, Estrov Z, Andreeff M, Cortes J E. Treatment with FLT3 inhibitor in patients with FLT3-mutated acute myeloid leukemia is associated with development of secondary FLT3-tyrosine kinase domain mutations. Cancer. 2014; 120: 2142-9

Choudhary C, Olsen J V, Brandts C, Cox J, Reddy P N, Bohmer F D, Gerke V, Schmidt-Arras D E, Berdel W E, Müller-Tidow C, Mann M, Serve H. Mislocalized activation of oncogenic RTKs switches downstream signaling outcomes. Mol Cell. 2009 Oct. 23; 36(2): 326-39

Barré B, Vigneron A, Coqueret O. The STAT3 transcription factor is a target for the Myc and riboblastoma proteins on the Cdc25A promoter. J Biol Chem. 2005 Apr. 22; 280(16): 15673-81

Hayakawa F, Towatari M, Kiyoi H, Tanimoto M, Kitamura T, Saito H, Naoe T. Tandem-duplicated Flt3 constitutively activates STAT5 and MAP kinase and introduces autonomous cell growth in IL-3-dependent cell lines. Oncogene. 2000 Feb. 3; 19(5):624-31

Mizuki M, Schwable J, Steur C, Choudhary C, Agrawal S, Sargin B, Steffen B, Matsumura I, Kanakura Y, Bohmer F D, Müller-Tidow C, Berdel W E, Serve H. Suppression of myeloid transcription factors and induction of STAT response genes by AML-specific Flt3 mutations. Blood. 2003 Apr. 15; 101(8):3164-73

Spiekermann K, Bagrintseva K, Schwab R, Schmieja K, Hiddemann W. Overexpression and constitutive activation of FLT3 induces STAT5 activation in primary acute myeloid leukemia blast cells. Clin Cancer Res. 2003 June; 9(6):2140-50

Nelson E A, Walker S R, Xiang M, Weisberg E, Bar-Natan M, Barrett R, Liu S, Kharbanda S, Christie A L, Nicolais M, Griffin J D, Stone R M, Kung A L, Frank D A. The STAT5 Inhibitor Pimozide Displays Efficacy in Models of Acute Myelogenous Leukemia Driven by FLT3 Mutations. Genes Cancer. 2012 July; 3(7-8):503-11

Yuan L L, Green A S, Bertoli S, Grimal F, Mansat-De Mas V, Dozier C, Tamburini J, Récher C, Didier C, Manenti S. Pim kinases phosphorylate Chk1 and regulate its functions in acute myeloid leukemia. Leukemia. 2014 February; 28(2):293-301

Paz-Priel I, Friedman A. C/EBPα dysregulation in AML and ALL. Crit Rev Oncog. 2011; 16(1-2):93-102

Bertero T, Gastaldi C, Bourget-Ponzio I, Mari B, Meneguzzi G, Barbry P, Ponzio G, Rezzonico R. CDC25A targeting by miR-483-3p decreases CCND-CDK4/6 assembly and contributes to cell cycle arrest. Cell Death Differ. 2013 June; 20(6):800-11.

Placke T, Faber K, Nonami A, Putwain S L, Salih H R, Heidel F H, Krämer A, Root D E, Barbie D A, Krivtsov A V, Armstrong S A, Hahn W C, Huntly B J, Sykes S M, Milsom M D, Scholl C, Fröhling S. Requirement for CDK6 in MLL-rearranged acute myeloid leukemia. Blood. 2014 Jul. 3; 124(1):13-23

Song Y, Lin X, Kang D, Li X, Zhan P, Liu X, Zhang Q. Discovery and characterization of novel imidazopyridine derivative CHEQ-2 as a potent CDC25 inhibitor and promising anticancer drug candidate. Eur J Med Chem. 2014 Jul. 23; 82:293-307

Caudill J S, Porchern J C, Steensma D P. Aberrant pre-mRNA splicing of a highly conserved cell cycle regulator, CDC25C, in myelodysplastic syndromes. Leuk. Lymphoma 2008, 49, 989-993.

Reikvam H, Tamburini J, Skrede S, Holdhus R, Poulain L, Ersvær E, Hatfield K J, Bruserud Ø. Antileukaemic effect of PI3K-mTOR inhibitors in acute myeloid leukaemia-gene expression profiles reveal CDC25B expression as determinate of pharmacological effect. Br. J. Haematol. 2014, 164, 200-211

Brenner A K, Reikvam H, Lavecchia A, Bruserud Ø. Therapeutic targeting the cell division cycle 25 (CDC25) phosphatases in human acute myeloid leukemia—the possibility to target several kinases through inhibition of the various CDC25 isoforms. Molecules. 2014, 19(11):18414-47.

Hanahan D, Weinberg R A. The hallmarks of cancer. Cell. 2000 Jan. 7; 100(1):57-70

Tenen D G. Disruption of differentiation in human cancer: AML shows the way. Nat Rev Cancer. 2003 February; 3(2):89-101

Schlenk R F, Döhner K, Krauter J, Fröhling S, Corbacioglu A, Bullinger L, Habdank M, Späth D, Morgan M, Benner A, Schlegelberger B, Heil G, Ganser A, Döhner H; German-Austrian Acute Myeloid Leukemia Study Group. Mutations and treatment outcome in cytogenetically normal acute myeloid leukemia. N Engl J Med. 2008 May 1; 358(18):1909-18

Patel J P, Gönen M, Figueroa M E, Fernandez H, Sun Z, Racevskis J, Van Vlierberghe P, Dolgalev I, Thomas S, Aminova O, Huberman K, Cheng J, Viale A, Socci N D, Heguy A, Cherry A, Vance G, Higgins R R, Ketterling R P, Gallagher R E, Litzow M, van den Brink M R, Lazarus H M, Rowe J M, Luger S, Ferrando A, Paietta E, Tallman M S, Melnick A, Abdel-Wahab O, Levine R L. Prognostic relevance of integrated genetic profiling in acute myeloid leukemia. N Engl J Med. 2012 Mar. 22; 366(12):1079-89

Patel J P, Levine R L. How do novel molecular genetic markers influence treatment decisions in acute myeloid leukemia? Hematology Am Soc Hematol Educ Program. 2012; 2012:28-34

Agresta S, Stein E M, Tallman M S, Levine R L, Yua H, Yen K, Fan B, Flinn I W, Fathi A T, Stone R M, DeAngelo D J, DeBotton S, Pollyea D A. A Phase I study of AG-221, a first in class, potent inhibitor of the IDH2-mutant protein in patients with IDH2 mutant positive advanced hematologic malignancies. EHA 2014, Abstract LB2434

Li L, Piloto O, Nguyen H B, Greenberg K, Takamiya K, Racke F, Huso D, Small D. Knock-in of an internal tandem duplication mutation into murine FLT3 confers myeloproliferative disease in a mouse model. Blood. 2008 Apr. 1; 111(7):3849-58.

Matsuo Y, MacLeod R A, Uphoff C C, Drexler H G, Nishizaki C, Katayama Y, Kimura G, Fujii N, Omoto E, Harada M, Orita K. Two acute monocytic leukemia (AML-M5a) cell lines (MOLM-13 and MOLM-14) with interclonal phenotypic heterogeneity showing MLL-AF9 fusion resulting from an occult chromosome insertion, ins(11; 9)(q23;p22p23). Leukemia. 1997 September; 11(9): 1469-77

Furet P, Bold G, Meyer T, Roesel J, Guagnano V. Aromatic interactions with phenylalanine 691 and cysteine 828: a concept for FMS-like tyrosine kinase-3 inhibition. Application to the discovery of a new class of potential antileukemia agents. J Med Chem. 2006 Jul. 27; 49(15):4451-4

Lazo J S, Nemoto K, Pestell K E, Cooley K, Southwick E C, Mitchell D A, Furey W, Gussio R, Zaharevitz D W, Joo B, Wipf P. Identification of a potent and selective pharmacophore for Cdc25 dual specificity phosphatase inhibitors. Mol Pharmacol. 2002 April; 61(4):720-8

Récher C, Beyne-Rauzy O, Demur C, Chicanne G, Dos Santos C, Mas V M, Benzaquen D, Laurent G, Huguet F, Payrastre B. Antileukemic activity of rapamycin in acute myeloid leukemia. Blood. 2005 Mar. 15; 105(6): 2527-34

Sanchez P V, Perry R L, Sarry J E, Perl A E, Murphy K, Swider C R, Bagg A, Choi J K, Biegel J A, Danet-Desnoyers G, Carroll M. A robust xenotransplantation model for acute myeloid leukemia. Leukemia. 2009 November; 23(11):2109-17

The invention claimed is:

1. A method of treating drug resistant acute myeloid leukemia (AML) associated with a FLT3-ITD mutation and/or for preventing tumor relapses in a patient suffering or having suffered from AML associated with a FLT3-ITD mutation, comprising
administering to the patient an effective amount of a CDC25A phosphatase inhibitor, wherein said CDC25A phosphatase inhibitor acts directly upon CDC25A phosphatase and said effective amount is sufficient to induce monocytic differentiation of AML cells.

2. The method according to claim 1, wherein said CDC25A phosphatase inhibitor is selected from the group consisting of a quinone derivative, a maleimide derivative and an inhibitor of CDC25A phosphatase expression.

3. The method of claim 1, wherein said CDC25A phosphatase inhibitor is IRC 083864.

4. The method of claim 1, further comprising administering to the patient a chemotherapeutic drug.

5. The method of claim 4, wherein the chemotherapeutic drug is an anti-mitotic agent.

* * * * *